(12) United States Patent
Buschmann et al.

(10) Patent No.: US 11,419,873 B2
(45) Date of Patent: *Aug. 23, 2022

(54) USE OF SODIUM CHANNEL BLOCKERS FOR THE TREATMENT OF NEUROPATHIC PAIN DEVELOPING AS A CONSEQUENCE OF CHEMOTHERAPY

(71) Applicant: Wex Medical Limited, Wanchai (HK)

(72) Inventors: Helmut Heinrich Buschmann, Barcelona (ES); Jose Miguel Vela Hernandez, Barcelona (ES); Jose Manuel Baeyens, Granada (ES)

(73) Assignee: WEX MEDICAL LIMITED, Kowloon (HK)

(*) Notice: Subject to any disclaimer, the term of this patent is extended or adjusted under 35 U.S.C. 154(b) by 0 days.

This patent is subject to a terminal disclaimer.

(21) Appl. No.: 16/786,789

(22) Filed: Feb. 10, 2020

(65) Prior Publication Data

US 2021/0252004 A1 Aug. 19, 2021

Related U.S. Application Data

(63) Continuation of application No. 16/264,155, filed on Jan. 31, 2019, now Pat. No. 10,624,896, which is a continuation of application No. 14/688,489, filed on Apr. 16, 2015, now abandoned, which is a continuation of application No. 12/294,843, filed as application No. PCT/EP2007/002662 on Mar. 26, 2007, now Pat. No. 9,018,222.

(30) Foreign Application Priority Data

Mar. 27, 2006 (EP) .................................. 06384006
Dec. 8, 2006 (EP) .................................. 06025476

(51) Int. Cl.

| | | |
|---|---|---|
| *A61K 31/529* | (2006.01) | |
| *A61K 31/337* | (2006.01) | |
| *A61K 31/475* | (2006.01) | |
| *A61K 31/517* | (2006.01) | |
| *A61K 31/52* | (2006.01) | |
| *A61K 33/243* | (2019.01) | |
| *A61K 33/24* | (2019.01) | |
| *A61K 45/06* | (2006.01) | |
| *A61K 31/519* | (2006.01) | |

(52) U.S. Cl.
CPC .......... *A61K 31/529* (2013.01); *A61K 31/337* (2013.01); *A61K 31/475* (2013.01); *A61K 31/517* (2013.01); *A61K 31/519* (2013.01); *A61K 31/52* (2013.01); *A61K 33/24* (2013.01); *A61K 33/243* (2019.01); *A61K 45/06* (2013.01)

(58) Field of Classification Search
CPC ... A61K 31/529; A61K 31/475; A61K 31/337
See application file for complete search history.

(56) References Cited

U.S. PATENT DOCUMENTS

| | | |
|---|---|---|
| 1,058,643 A | 4/1913 | Tahara |
| 3,898,339 A | 8/1975 | Adams et al. |
| 4,022,899 A | 5/1977 | Adams et al. |
| 4,029,793 A | 6/1977 | Adams et al. |
| 5,688,830 A | 11/1997 | Berger et al. |
| 5,846,975 A | 12/1998 | Pan et al. |
| 6,030,974 A | 2/2000 | Schwartz et al. |
| 6,407,088 B1 | 11/2002 | Dong et al. |
| 6,478,966 B2 | 11/2002 | Zhou et al. |
| 6,552,191 B1 | 4/2003 | Zhou et al. |
| 6,559,154 B2 | 5/2003 | Kang et al. |
| 6,562,968 B2 | 5/2003 | Zhou et al. |
| 6,599,906 B1 | 7/2003 | Ku et al. |
| 6,780,866 B2 | 8/2004 | Ku et al. |
| 7,125,908 B2 | 10/2006 | Ehring et al. |
| 2002/0198226 A1 | 12/2002 | Ku et al. |
| 2004/0214842 A1 | 10/2004 | Ku et al. |
| 2005/0014844 A1 | 1/2005 | Gaida et al. |
| 2005/0014847 A1 | 1/2005 | Gaida et al. |
| 2005/0020610 A1 | 1/2005 | Zhang et al. |
| 2009/0105197 A1 | 4/2009 | Ku et al. |
| 2009/0143415 A1 | 6/2009 | Buschmann et al. |

FOREIGN PATENT DOCUMENTS

| | | |
|---|---|---|
| CN | 1145225 A | 3/1997 |
| CN | 1192903 C | 9/1998 |
| CN | 1227102 C | 9/1999 |
| CN | 1356104 A | 7/2002 |
| EP | 0750909 B1 | 12/2002 |
| EP | 1702627 A1 | 9/2006 |
| GB | 1370904 A | 10/1974 |
| KR | 20020091641 A | 12/2002 |
| RU | 2223758 C1 | 2/2004 |

(Continued)

OTHER PUBLICATIONS

Keskinbora et al. "Gabapentin and an Opioid Combination Versus Opioid Alone for the Management of Neuropathic Cancer Pain: A Randomized Open Trial" Journal of Pain and Symptom Management, 2007, 34, 183-189.

(Continued)

*Primary Examiner* — Shobha Kantamneni
(74) *Attorney, Agent, or Firm* — Fox Rothschild LLP

(57) ABSTRACT

The present invention refers to the use of sodium channel blockers such as tetrodotoxin or saxitoxin, its analogues/derivatives as well as their acceptable salts, for the production of a medicament for the treatment of neuropathic pain resulting from chemotherapy.

16 Claims, 8 Drawing Sheets

(56) References Cited

FOREIGN PATENT DOCUMENTS

| WO | 98051290 A2 | 11/1998 |
|---|---|---|
| WO | 02022129 A1 | 3/2002 |
| WO | 02041915 A1 | 5/2002 |
| WO | 02094272 A1 | 11/2002 |
| WO | 03037890 A2 | 5/2003 |
| WO | 03097691 A1 | 11/2003 |
| WO | 04024061 A2 | 3/2004 |
| WO | 05042497 A3 | 5/2005 |
| WO | 06032459 A1 | 3/2006 |
| WO | 06032481 A1 | 3/2006 |

OTHER PUBLICATIONS

Kohane et al., "A Re-examination of Tetrodotoxin for Prolonged Duration Local Anesthesia," Anesthesiology, vol. 89, Issue 1, pp. 119-131 (Jul. 1998).
Koppert et al., "Low-dose Lidocaine Reduces Secondary Hyperalgesia by a Central Mode of Action," Pain, vol. 85, No. 1-2, pp. 217-224 (Mar. 2000).
Kukkar et al. "Implications and mechanism of action of gabapentin in neuropathic pain". Arch. Pharm. Res. (2013) 36: 237-251.
Laird et al., "Deficits in Visceral Pain and Referred Hyperalgesia in NAVI .8 (SNS/PN3)-Null mice", Journal of Neuroscience, The Society, Washington, DC, US, vol. 22, No. 19, Oct. 2002. pp. 8352-8356.
Lin et al., "Preparation ofQuananlin (1 µg/MI and 10 µG/MI TIX) According to Wang's Process as per CN1145225," Research Findings of Nanning Maple Leaf Pharmaceutical Co. 3Ltd., pp. 1-9, Nov. 23, 2003.
Lin, Declaration of Weiyang Lin, Ph.D., European Patent Appl. 01982091.8, 5 pp., dated Apr. 20, 2007.
Lin, Declaration of Weiyang Lin, Ph.D., U.S. Appl. No. 90/007,826 (Reexamination of U.S. Pat. No. 6,407,088), pp. 17, dated May 27, 2007.
Lu et al., "Tetrodotoxin TIX Analgesic Effect as assessed with Different Experimental Animal Models," Poster Presentation, 31st Society for Neuroscience Annual Meeting, 1 page, Nov. 2001.
Lyrica™ (pregabalin) product monograph {2012), 49 pp., RefID No. 3148643.
Lyu, "Low Dose of Tetrodotoxin Reduces Neuropathic Pain Behaviours in an Animal Model," Brain Research 871, pp. 98-103 (2000).
Mosher, "The Chemistry of Tetrodotoxin," Annals of the New York ?cademy of Sciences, 479:32-43 (1985).
Neurontin® (gabapentin) product monograph (2013), 37 pp., RefID No. 3301312.
Ngoc, Declaration of Ngoc, Anh Ho Ngoc, European Patent Appl. 01982091.8, 8 pp., dated Apr. 26, 2006.
Noguchi "Fugu (Pufferfish) Poison" NHK Books, Ch. 1, pp. 46-53 (1996).
Omana-Zapata et al., "Tetrodotoxin Inhibits Neuropathic Ectopic Activity in Neuromas, Dorsal Root Ganglia and Dorsal Hom Neurons," Pain, vol. 72, pp. 41-49 (1997).
Ossipov et al., "Challenges in the development of Novel Treatment Strategies for Neuropathic Pain," Neuro Rx: Journal of the American Society for Experimental Neurotherapeutic vol. 2, No. 4,pp. 650-661,2005.
Patarica-Huber et al., "Multimodal Approach to Therapy-Related Neuropathic Pain in Breast Cancer" Official Journal of the Balkan Union of Oncology (BUON), 2011, 16, 40-45 (Abstract).
Rao et al, 'Efficacy of Lamotrigine in the Management of Chemotherapy-induced Peripheral Neuropathy.' Cancer, vol. 112, No. 12, pp. 2802-2808, Jun. 15, 2008.
Rao et al., "Efficacy of Gabapentin in the Management of Chemotherapy-induced Peripheral Neuropathy," Cancer, 2007, 110(9), 2110-2118.
Rose, "Nicotine Addiction and Treatment," Annual Review of Medicine, vol. 47, pp. 493-507 (1996).
Ross et al. "Gabapentin is Effective in the Treatment of Cancer-Related Neuropathic Pain: A Prospective, Open-Label Study". Journal of Palliative Medicine, vol. 8, No. 6, 2005 nn. 1118-1126.
Sabatowski, Declaration of Rainer Sabatowski, European Patent Appl. 01982091.8, 23 pp., dated Dec. 1, 2003.
Sankyo Co. Ltd., Advertisement and Label for marketed Tetrodotoxin; "Pure Puffer Fish Poison Tetrodoxin", Journal of Neurology, 3 pp., 1931.
Serpell et al., "Gabapentin in neuropathic pain syndroms: A randomized, double-blind, placebo-controlled trial" Pain, 2002, 99, 557-566.
Suehiro, "Historical Review on the Chemical and Medical Studies of Globefish Toxin Before World War II," I Soc. Hist Pharmacy, 29:428-434 (1994).
Takahashi et al., A Prospective Open-label Trial of Gabapentin as an Adjuvant Analgesic with Opioids for Japanese Patients with Neuropathic Cancer Pain. Int J. Clin. Oncol., 2010,15,46-51,Abstract.
Tsavaris, et al. "Gabapentin Monotherapy for the Treatment of Chemotherapy-Induced Nueropathic Pain: A Pilot Study" Pain Medicine, 2008, 9(8), 1209-1216.
U.S. Patent and Trademark Office, Second Non-final Office Action (withdrawal and replacement dated Jun. 12, 2007 Office Action), U.S. Appl. No. 90/007,826 (Re-examination of U.S. Pat. No. 6,407,088, Jul. 2007.
U.S. Department of Health and Human Service, Food and Drug Administration, Center for Drug Evaluation and Research, "Guidance for Industry Estimating the Maximum Safe Starting Dose", 30 pp., Dec. 2002.
U.S. Patent and Trademark Office, Final Office Action, U.S. Appl. No. 90/007,826 (Reexamination of U.S. Pat. No. 6,407,088), 38 pp., dated Feb. 21, 2007.
U.S. Patent and Trademark Office, Non-final Office Action, U.S. Appl. No. 90/007,826 (Reexamination of U.S. Pat. No. 6,407,088), 4 pp., dated Dec. 22, 2006.
U.S. Patent and Trademark Office, Non-final Office Action, U.S. Appl. No. 90/007,826 (Re-examination of U.S. Pat. No. 6,407,088), 33 pp., dated Jul. 24, 2006.
U.S. Patent and Trademark Office, Non-final Office Action, U.S. Appl. No. 11/663,268, 16 pp., dated Oct. 19, 2009.
U.S. Patent and Trademark Office, Office Communication—reasons for patentability, U.S. Appl. No. 90/007,826—(Re-examination of U.S. Pat. No. 6,407,088), 9 pp., dated Jan. 23, 2008.
U.S. Patent and Trademark Office, Order Granting Ex Parte Reexam, U.S. Appl. No. 90/007,826 (Re-examination of U.S. Pat. No. 6,407,088), 14 pp., dated Jan. 19, 2006.
U.S. Patent and Trademark Office, Second final Office Action, U.S. Appl. No. 90/007,826 (Reexamination of U.S. Pat. No. 6,407,088), 27 pp., dated Jun. 12, 2007.
Vadalouca et al. "Pharmacological Treatment of Neuropathic Cancer Pain: A Comprehensive Review of the Current Literature". Pain Practice, vol. 2, Issue 3, 2012, 219-251.
Vippagunta et al. "Crystalline solids" Advanced Drug Delivery Reviews 48 (2001) 3-26.
Vogal et al., "Drug Discovery and Evaluation—Pharmacology Assays," Science Publishing (2001), 5 pp., (Translation Included).
Wallace, "Calcium and Sodium Channel Antagonists for the Treatment of Pain," Clinical Journal of Pain, vol. 16, pp. S80-S85 (2000).
Wolf et al., Chemotherapy-Induced Perpheral Neuropathy: Prevention and Treatment Strategies; Eur. I Cancer, 2008, 44, 1507-1515.
Xiao et al., "Chemotherapy-Evoked Painful Peripheral Neuropathy: Analgesic Effects of Gabapentin and Effects on Ex? ression of the A!pha-2-Delta Type-I Calcium Channel Subunit" Neuroscience, 2007, 144(2), pp. 714-720.
XP002332723, Database WPI, Section Ch, Week 200111, abstract of Chinese Patent Application Publication No. CNI 145225, Thomson Scientific, London, GB, AN 2001-09219.
Xu et al., "Influence of Tetrodotoxin on Sodium Channel and the Possible Mechanism of the Analgesic Effect," Chinese Pharmacological Bulletin, nn.249-252 (2003).
Yoshimura et al., "The Involvement of the Tetrodotoxin-Resistant Sodium Channel Nav1.8 (PN3/SNSJ in a Rat Model of Visceral Pain", Journal of Neuroscience, New York, NY, US, V vol. 21, ov.2001, pp. 8690-8696.

(56) References Cited

OTHER PUBLICATIONS

Yotsu et al., "An Improved Tetrodotoxin Analyzer," Agric. Biol. Chem., 53 (3):893-895 (1989).
Yotsu-Yamashita, "Chemistry of Puffer Fish Toxin," I Toxicol—ToxinReview, 20(1):51-66, (2001).
Yu et al., "Experimental Study on the Analgesic Effect of Tetrodotoxin in Mice," Acta. Acadamae Medicinae Shandong; 37: 1 20-12, Jun. 1999.
Zhang et al., "Pharmacology," People's Hygiene Publishing, vol. 1, pp. 389, (1965).
Abdelsayed and Sokolov, "Voltage-gated sodium channels," Channels, Jun. 2013, 7(3): 146-152.
Clinckers et al., "Hippocampal dopamine and serotonin elevations as phannacodynamics markers for the antivconvulsant efficacy of oxcarbazepine and 10,11-dihydro-10-hydroxycarbamazepine," Neuroscience Letters, 2005, 48-53.
Dailey et al., "Carbamazepine-Induced Release of Serotonin from Rat Hippocampus In Vitro," Epilepsia, 1998, 39(10): 1054-1063.
Dardis et al., "Fatal Serotonin Syndrome Precipitated by Oxcarbazepine in a Patient Using an Selective Serotonin Reuptake Inhibitor," The Neurologist, Jul. 2012, 18(4): 204-205.
Elphick et al., "Effects of Carbamazepine on Dopamine- and Serotonin-Mediated Neuroendocrine Responses," Arch. Gen. Psvchiatrv, Febmarv 1990, 47: 135-140.
Lavoie et al., "Effect ofDuloxetine on Pain, Function, and Quality of Life Among Patients With Chemotherapy-Induced Painful Peripheral Neuropathy," JAMA, Apr. 2013, 1359-1367.
Lema et al., "Types and Epidemiology of Cancer-Related Neuropathic Pain: The Intersection of Cancer Pain and Neuropathic Pain," The Oncologist, 2010, 3-8.
Moczydlowski, "The molecular mystique of tetrodotoxin," Toxicon, 2012, 1-9.
Nozaki-Taguchi et al., "Vincristine-induced allodynia in the rat," Pain, 2001, 69-76.
Xiao et al., "Experimental Studies of Potential Analgesics for the Treatment of Chemotherapy-Evoked Painful Peripheral Neuropathies," Pain Medicine, 2008, 9(5): 505-517.
Jung et al., "Neuropathic Pain Associated with Non-surgical Treatment of Breast Cancer," Pain, vol. 118, No. 1-2, pp. 10-14, Nov. 2005.
Birch, Stewart, Kolasch & Birch, LLP, Applicant's Response to Final Office Action dated Feb. 21, 2007, U.S. Appl. No. 90/007,826 (Re-examination of U.S. Pat. No. 6,407,088), 29 pp., filed Apr. 23, 2007.
U.S. Department of Health and Human Services, Food and Drug Administration, Center for Drug Evaluation and Research, Center for Biologics and Evaluation and Research, "Guidance for Industry and Reviewers Estimating the Safe Starting Dose in Clinical Trials for Therapeutics in Adult Healthy Volunteers," 30 pp., Dec. 2002.
Hashiguchi et al., "Characterization and evolutionary analysis of tributyltin-binding protein (TBT-bp) and pufferfish saxitoxin and tetrodotoxin binding protein (PSTBP) genes in toxic and non-toxic pufferfishes", J. Evol Biol, May 2015, vol. 28, pp. 1103-1118.
Kudo et al., Isolation of 6-Deoxytetrodotoxin from the Pufferfish, Takifugu pardalis, and a Comparison of the Effects of the C-6 and C-11 Hydroy Groups of Tetrodotoxin on It. Mar. 2014.
Nakatani et al., The Contents and Composition of Tetrodotoxin and Paralytic Shellfish Poisoning Toxins in Marine Pufferfish *Canthigaster rivulata:*, Shokuhin Eiseigaku Zasshi.
Various Authors, "Neuropathies 2". Clinical Neurophysiology, Elsevier Science, IE, vol. 111, ISSN 1388-2457, pp. S41-S44, (2000), XP027216056.
Adelspberger et al., "The Chemotherapeutic Oxaliplatin Alters Voltage-gated Na+ Channel Kinetics 25-32, on Rat 2000 Sensory Neurons," European Journal of Pharmacology, vol. 406, No. I, pp. 25-32, 2000.
Anger, et al., "Medicinal Chemistry of Neuronal Voltage-Gated Sodium Channel Blockers," 2001 Journal of Medicinal Chemistry, American Chemical Society, vol. 44, No. 2, Jan. 18, 2001.

Arai et al. "Low-dose gabapentin as useful adjuvant to opioids for neuropathic cancer pain when combined with low-dose imipramine" J Anesth., 2010, 24, 407-410.
Beyak et al., "Inflammation-induced hyperexcitability of nociceptive gastrointestinal DRG neurones: the role of voltage-gated ion channels", Neurogastroenterology and Motility, Blackwell Publishing Ltd, vol. 17, No. 2, Apr. 2005, 175-186.
Birch et al., "Strategies to Identify Ion Channel Modulators: Current and Novel Approaches to Target Neuropathic Pain," DDT—Drug Discovery Today, vol. 9, No. 9, pp. 410-418, May 2004.
Birch, Stewart, Kolasch & Birch, LLP, Applicant's Request for Re-examination, U.S. Appl. No. 90/007,826 (Re-examination of U.S. Pat. No. 6,407,088), 36 pp., filed Nov. 2.
Birch, Stewart, Kolasch & Birch, LLP, Applicant's Response to Non-Final Office Action dated Jul. 16, 2007, U.S. Appl. No. 90/007,826 (Re-examination of U.S. Pat. No. 6,407,088).
Birch, Stewart, Kolasch & Birch, LLP, Applicant's Response to Office Action dated Jul. 24, 2006 and Notice of Defective Paper of Dec. 22, 2006, U.S. Appl. No. 90/007,826.
Birch, Stewart, Kolasch & Birch, LLP, Applicant's Response to Office Action dated Jul. 24, 2006, U.S. Appl. No. 90/007,826 (Re-examination of U.S. Pat. No. 6,407,088), 83 pp., filed Sep. 21, 2006.
Birch, Stewart, Kolasch & Birch, LLP, Applicant's Response to Order Granting Ex Parle Re-examination of Jan. 19, 2006, U.S. Appl. No. 90/007,826 (Re-examination of U.S. Pat. No. 6,407,088, 10 pp., filed Mar. 20, 2006.
Bower et al., "Nonprotein Neurotoxins," Clinical Toxicology, 18(7), pp. 813-863 (1981).
Caraceni et al., "Gabapentin for Neuropathic Cancer Pain: A Randomized Controlled Trial from the Gabapentin Cancer Pain Study Group" J. Clin. Oneal., 2004, 22(14), 2909-2917.
Cersosimo, "Oxaliplatin-Associate Neuropathy: A Review," The Annals of Pharmacotherapy, vol. 39, pp. 128-135, Jan. 2005.
Chen, "Pharmacology on Clinical Anesthesia," People's Hygiene Publishing, 1st Edition, pp. 330, Jul. 2000.
Chen, "Method on the Pharmacology Researching of Chinese Medicine," People's Hygiene Publishing, 1st Edition, pp. 1103-1104, Sep. 2003.
Cleland et al., Assessment of Cancer-Related Neuropathy and Neuropathic Pain, Oncologist, 2010, 15(suppl. 2), 13-18.
Clinical Trials.gov A study of Sativex® for Pain Relief in Patients with Advanced Malignancy (SPRAY), updated Jun. 13, 2013, 4pp.
Cymbalta® product monograph (2004, revised 2012) 28 pp. Ref ID No. 3205434.
Database VVPI Week 200334, Derwent Publications Ltd., London, GB; AN-2003-360529 & KR 2002 091 641 A (Kim Is), 5 pp., Dec. 6, 2002.
Devulder et al., "Central Pain: an overview," ACTA Neurologica Belgica, Belgium, vol. 102, No. 3, pp. 97-103 (2002).
Du Sovich, Declaration of Patrick du Souich, European Patent Appl. 01982091.8, 3 pp., dated Apr. 4, 2007.
Du Sovich, Declaration of Patrick du Souich, European Patent Appl. 01982091.8, 63 pp., dated Dec. 8, 2003.
Du Sovich, Declaration of Patrick du Souich, U.S. Appl. No. 90/007,826 {Reexamination of U.S. Pat. No. 6,407,088), 7 pp. , dated Sep. 12, 2007.
Du Sovich, Declaration of Patrick du Souich, U.S. Appl. No. 90/007,826 (Reexamination of U.S. Pat. No. 6,407,088), 53 pp. , dated Sep. 21, 2006.
Dworkin et al., Advances in Neuropathic Pain, Arch. Neural., 2003, 60, 1524-1534.
Dworkin et al., Pharmacologic Management of Neuropathic Pain: Evidence-Based Recommendations, Pain, 2007, 132, 237-251.
Dworkin et al., Recommendations for the Pharmacological Management of Neuropathic Pain: An Overview and Literature Update, Mayo Clin. Proc., 2010, 85(3){suppl.), S3-SI4.
Eckel et al., "Prophylaxe der Oxaliplatin-indurierten Neuropathie mit Carbamazepin" Deutsche Medizinische Wochenschrift, Germany, vol. 127, No. 3, pp. 78-82, (2002) (Translation of Introduction).

(56) References Cited

OTHER PUBLICATIONS

European Patent Office, Communication dated Jul. 30, 2010 with Supplementary European Search Report for European Appln. No. 06802402.5 (9 DD.).
European Patent Office, European Search Report dated Oct. 12, 2011 for EPI 1180427, 13 pp.
European Search Report, EP 10180006,8, dated Jan. 31, 2011.
Evans "Mechanism of Saxttoxin and Tetrodotoxin Poisoning," Brit Med. Bull., 1969, 25(3), 263-267.
Food & Drug Administration of USA, "Table I Conversion of Animal Doses to Human Equivalent Doses (HED) Based on Body Surface Area," 1 page, Sep. 15, 1998.
Gaida et al., "Ambroxol, a Nav1.8-preferring NA+ channel blocker, effectively suppresses pain symptoms in animal models of chronic, neuropathic and inflammatory pain", Neuropharmacology, Pergamon Press, vol. 49, No. 8, Dec. 2005, pp. 1220-1227.
Goodman et al., The Pharmacological Basis of Therapeutics, 8th Edition, NY, p. 54, (1990).
Habermann, Hruschka & Schnabel, Applicant's Grounds of Appeal filed in European Patent Application01982091.9, 60 pp., filed Jun. 12, 2004.
Haegerstam, "Effect of IV Administration of Lignocaine and Tetrodotoxin on Sensory Units in the Tooth of the Cat," Br. I Anaesth. 51:487-491 (1979).

Hagen et al., "An Open Label, Multi-Dose Efficacy and Safety Study of Intramuscular Tetrodototoxin in Paitents with Severe Cancer-Related Pain", Journal of Pain and Symptom Management, pp. 171-182, 2007.
Hershman et al. "Prevention and Management of Chemotherapy-Induced Peripheral Neuropathy in Survivors of Adult Cancers: American Society of Clinical Oncology Clinical Practice Guideline" J. Clin. Oncol., 2014 pp. 1941-1967.
Hong, Declaration of Geng-Xim Hong, European Patent Appl. 01982091.8, 90 pp., dated Jun. 12, 2004.
Huang, Declaration of Renbing Huang, European Patent Appl. 01982091.8, 5 pp., dated May 29, 2007.
Huang, "Validation Study of the Analgesic Effect of Quananlin," document submitted in European Patent Appl. 01982091.9, 6 pp., Dec. 11, 2003.
Johnson et al., (2010) Multicenter, Double-Blind, Randomized, Placebo-Controlled, Parallel-Group Study of the Efficacy, Safety, and Tolerability of THC:CBD Extract and THC E Journal of Pain and Symptom Management, 2010, 167-179.
Kaley et al., Therapy of Chemotherapy-Induced Peripheral Neuropathy, Brit I Haematology, 2009, 145, 3-14.
Kao et al., "Pharmacological Studies on Tarichatoxin, a Potent Neurotoxin," F.A, I Pharmacol, 140: 31-40, Dec. 26, 1962.
Kao, "Tetrodotoxin, Saxitoxin and their Significance in the Study of Excitation Phenomena," Pharmacological Reviews, vol. 18, No. 3, pp. 997-1049 (1966).

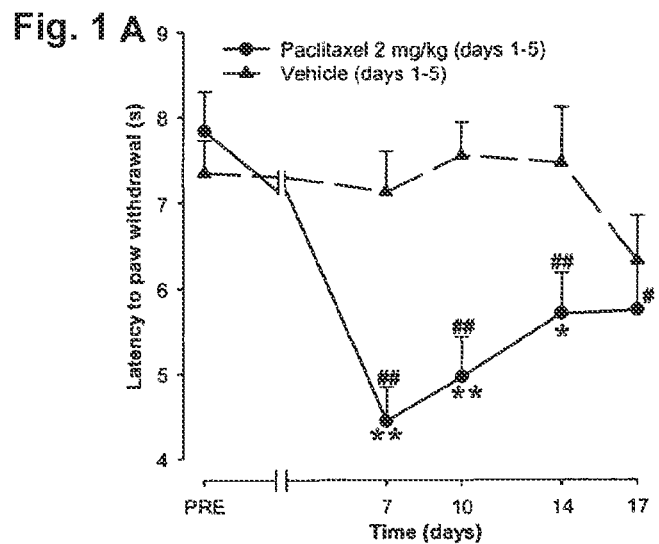
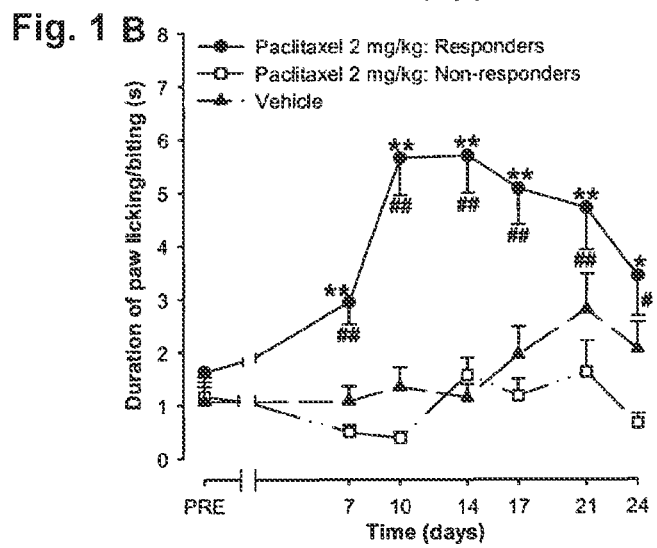
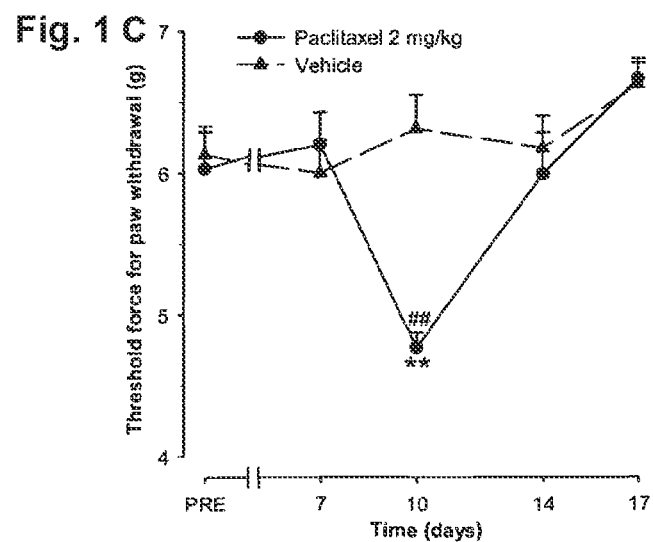

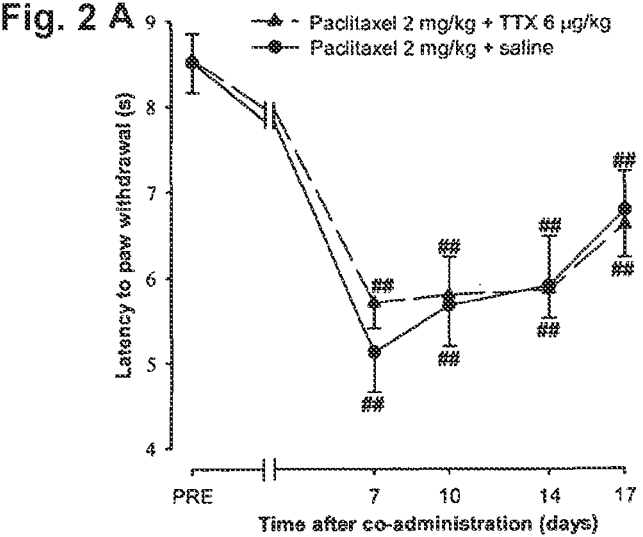
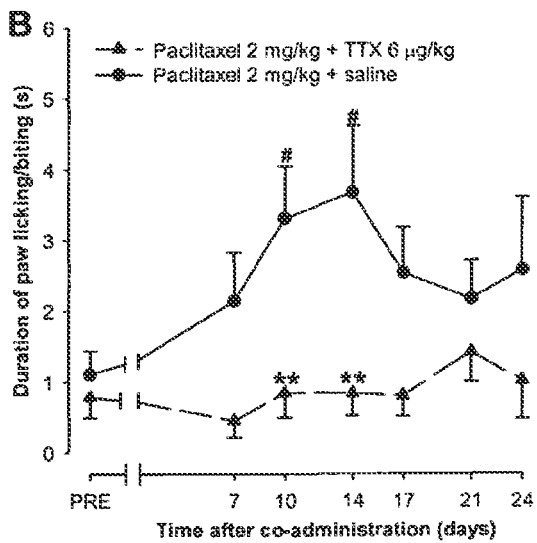
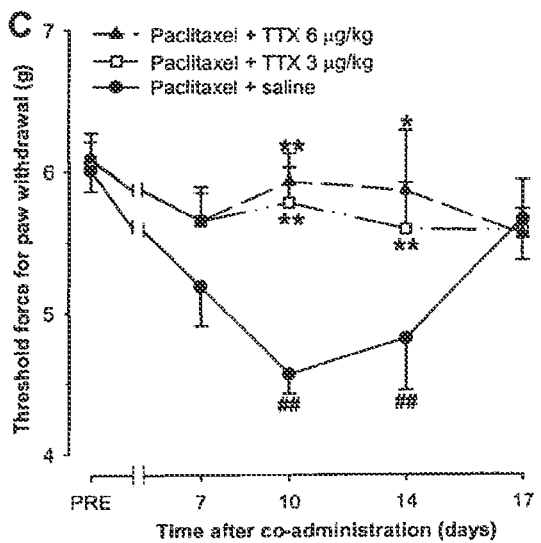

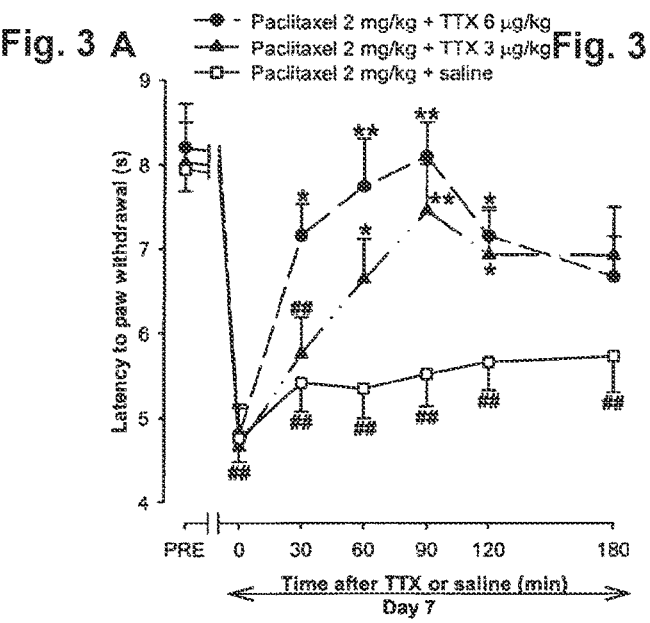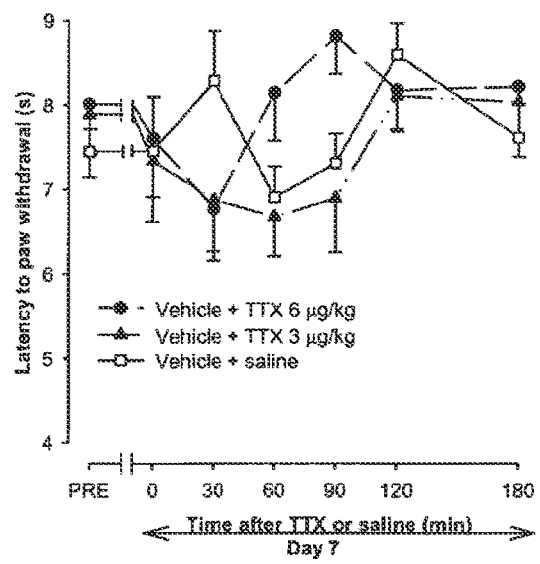

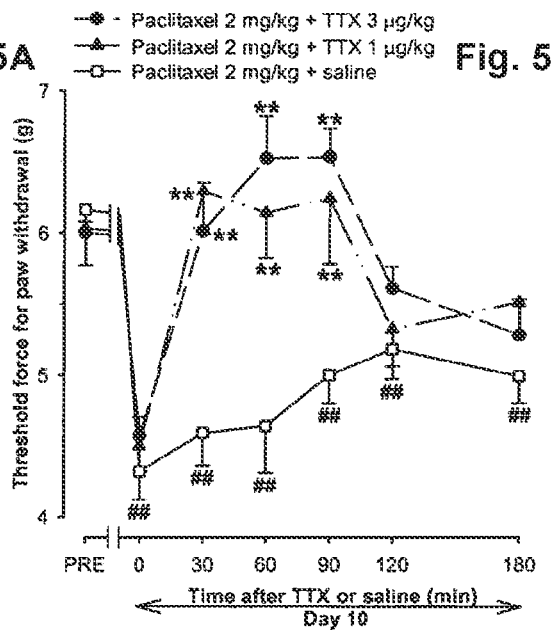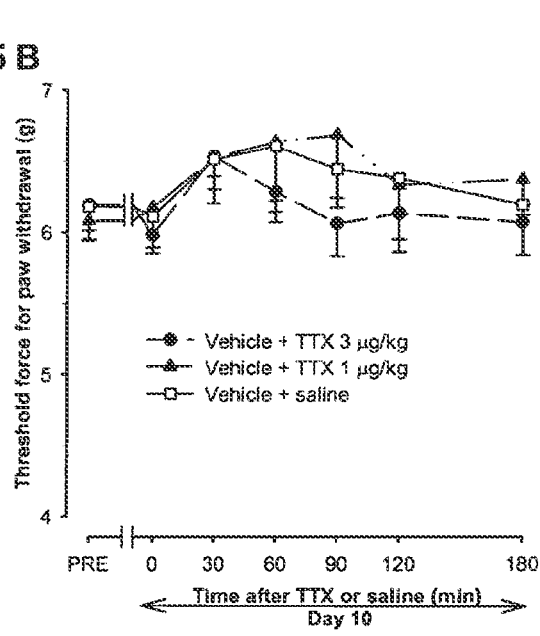

USE OF SODIUM CHANNEL BLOCKERS FOR THE TREATMENT OF NEUROPATHIC PAIN DEVELOPING AS A CONSEQUENCE OF CHEMOTHERAPY

CROSS-REFERENCE TO RELATED APPLICATIONS

This is a continuation of U.S. application Ser. No. 12/294,843, filed Jun. 30, 2009, which national phase under 35 U.S.C., 371 of International Application Number PCT/EP2007/002662, filed internationally on Mar. 26, 2007 which claims the benefit of European Application Number 06384006.0, filed Mar. 27, 2006 and European Application Number 06025476.0, filed Dec. 8, 2006. The related applications are hereby incorporated by reference.

FIELD OF THE INVENTION

The present invention refers to the use of sodium channel blockers such as tetrodotoxin or saxitoxin, its analogues/derivatives as well as their acceptable salts, for the production of a medicament for the treatment of neuropathic pain resulting from chemotherapy.

BACKGROUND OF THE INVENTION

The treatment of pain conditions is of great importance in medicine. There is currently a world-wide need for additional pain therapy. The pressing requirement for a specific treatment of pain conditions or as well a treatment of specific pain conditions which is right for the patient, which is to be understood as the successful and satisfactory treatment of pain for the patients, is documented in the large number of scientific works which have recently and over the years appeared in the field of applied analgesics or on basic research on nociception.

PAIN is defined by the International Association for the Study of Pain (IASP) as "an unpleasant sensory and emotional experience associated with actual or potential tissue damage, or described in terms of such damage (IASP, Classification of chronic pain, $2^{nd}$ Edition, IASP Press (2002), 210). Even though pain is always subjective its causes or syndromes can be classified. Especially neuropathic pain which in the past years has developed into a major health problem in broad areas of the population needs a very specific treatment, especially considering that any treatment of neuropathic pain is extremely sensitive to the causes behind the pain, be it the agent/disease ultimately causing it or the mechanistic pathway over which it develops. So, in a majority of cases a substance being able to treat one subtype of neuropathic pain is not—or is at least not necessarily—able to treat other specific subtypes due to the highly diverse nature of this generalized symptom called neuropathic pain.

On the other hand cancer and the therapy thereof are one of the biggest health concerns in the world. Besides surgery and close to allways supplementing it chemotherapy is the method of choice for controlling or helping patients struck by carcinomas.

Chemotherapy is the use of chemical substances to treat disease and in the sense of this invention refers primarily to the use of cytotoxic drugs (called chemotherapeutic drugs) to treat cancer. Chemotherapy 'in cancer consists of a personalized combination of potent chemotherapy drugs, designed to slow rapid cancer tumor growth, shrink tumors, kill cancer cells, and prevent the spread of cancer. The chemotherapeutic drugs prevent cells from replicating in the typical, out-of-control manner in which cancer cells divide.

Peripheral neurotoxicity is a clinically significant complication of cancer chemotherapy. For several of the most effective drugs (e.g. taxanes, vincristine, cisplatin), neurotoxicity is dose-limiting and sometimes forces the termination of otherwise successful therapy (Polomano and Bennett, 2001). Since these drugs are the treatment of choice for a multitude of lymphoid and solid tumours, hundred of thousands of patients each year are affected, Sensory abnormalities from antineoplastic-evoked neurotoxicity range from mild paresthesiae or dysesthesiae in many patients to a chronic painful peripheral neuropathy in a subset (Quasthoff and Hartung, 2002). The occurrence and severity of the neuropathy is dependent on single dose intensity, duration of treatment, cumulative dose, prior or concurrent treatment with other neuropathic drugs and co-existing conditions such as diabetes and alcohol abuse (Alberts et al., 1995; Postma et al., 1995; Forsyth et al., 1997; Quasthoff and Hartung, 2002). Thus it is known that as a result of Chemotherapy in a considerable number of cases neuropathic pain/allodynia/hyperalgesia develops. This is a very specific, development of symptoms coming from neurotoxicity of the chemotherapeutic drug and treatment of that is crucial for assuring quality of live.for patients suffering these consequences of chemotherapy.

Therefore. the objective of the present invention was to provide a new form of treatment for neuropathic pain/allodynia/hyperalgesia developing as a consequence of Chemotherapy.

BRIEF DESCRIPTION OF THE FIGURES

FIG. 1A is a graphical depiction of a time-course of paclitaxel induced thermal hyperalgesia, cold-allodynia, and mechanical allodynia on latency to paw withdrawal in mice.

FIG. 1B is a graphical depiction of a time-course of paclitaxel induced thermal hyperalgesia, cold-allodynia, and mechanical allodynia on duration of paw licking/biting in mice.

FIG. 1C is a graphical depiction of a time-course of paclitaxel induced thermal hyperalgesia, cold-allodynia, and mechanical allodynia on threshold force for paw withdrawal in mice.

FIG. 2A is a graphical depiction of a time-course of the effect of co-administration of paclitaxel and tetrodotoxin or paclitaxel and saline on latency to hind paw withdrawal in the plantar test.

FIG. 2B is a graphical depiction of a time-course of the effect of co-administration of paclitaxel and tetrodotoxin or paclitaxel and saline on the duration of hind paw licking/biting in the acetone test.

FIG. 2C is a graphical depiction of a time-course of the effect of co-administration of paclitaxel and tetrodotoxin or paclitaxel and saline on threshold force for hind paw withdrawal in the Von Frey test.

FIG. 3A is a graphical depiction of a time-course of the effect on the latency to hind paw withdrawal (plantar test) of a single s.c. injection of tetrodotoxin or saline in mice pretreated with paclitaxel.

FIG. 3B is a graphical depiction of a time-course of the effect on the latency to hind paw withdrawal (plantar test) of a single s.c. injection of tetrodotoxin or saline in mice pretreated with paclitaxel-vehicle.

FIG. 5A is a graphical depiction of a time-course of the effect on the threshold force for hind paw withdrawal (Von Frey test) of a single s.c. injection of tetrodotoxin or saline in mice pre-treated with paclitaxel.

FIG. 5B is a graphical depiction of a time-course of the effect on the threshold force for hind paw withdrawal (Von Frey test) of a single s.c. injection of tetrodotoxin or saline in mice pre-treated with paclitaxel-vehicle.

DESCRIPTION

Figure 4A:
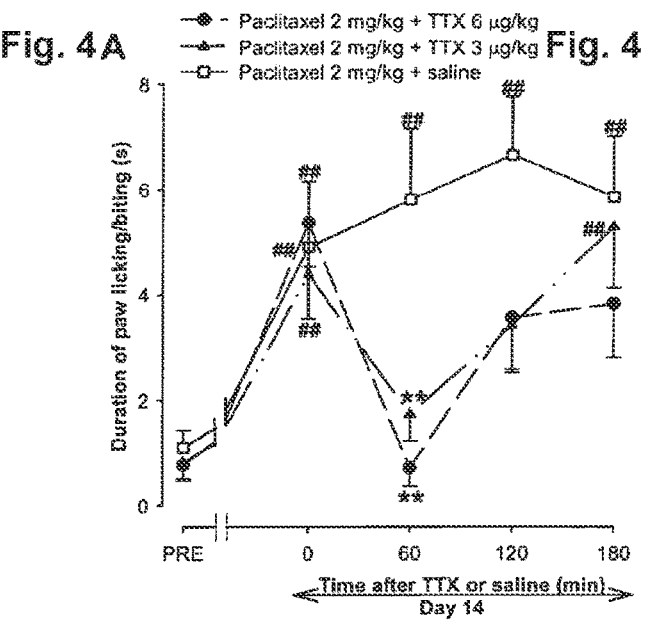
FIG. 4A is a graphical depiction of a time-course of the effect on the duration of hind paw licking/biting (acetone test) of a single s.c. injection of tetrodotoxin or saline in-mice pretreated with paclitaxel.

It is surprising that administration of TTX is highly effective for the treatment for neuropathic pain/allodynia/hyperalgesia developing after Chemotherapy.

Thus, the present invention relates to the use of sodium channel Mockers such as TTX or STX, its analogues/derivatives, optionally in the form of its racernate, pure stereoisomers, especially enantiomers or diastereomers or in the form of mixtures of stereoisomers, especially enantiomers or diastereomers, in any suitable mixing ratio; in neutral form, in the form of an acid or base or in form of a salt, especially a physiologically acceptable salt, or in form of a solvate, especially a hydrate for the production of a rmidicament for the treatment of neuropathic pain developing as a consequence of Chemotherapy.

"Chemotherapy" in the sense of this invention is defined as the use of a chemotherapeutic drug for the treatment of cancer or 'tumors or malign neoplasia respectively.

"Developing as a consequence of Chemotherapy" according to this invention is defined as a) developing after or with the initiating of Chemotherapy and b) thus coinciding with or following the use of a chemotherapeutic drug. Therefore the symptom to be treated—in all scientific likelihood—is being caused by or is due to the to toxicity/citotoxiolty, especially the neurotoxicity, of the chemotherapeutic drug.

"Chemotherapeutic drugs in the sense of this invention are compounds used in chemotherapy, especially those working by impairing mitosis (cell division), effectively targeting fast-dividing cells. As these drugs cause damage to cells they are termed cytotoxic. Some drugs cause cells to undergo apoptosis (so-called "cell suicide"). Especially preferred chemotherapeutic drugs in the sense of this invention are drugs derived from platin, especially the platin-derivatives cisplatin, carboplatin and oxaliplatim plant alkaloids and terpenes (terpenoids).

"Plant alkaloids" (and terpenoids) are alkaloids derived from plants and block cell division by preventing microtubule function. Microtubules are vital for cell division and without them it can not occur. The main examples are *Vinca* alkaloids and taxanes.

"*Vinca* alkaloids" bind to specific sites on tubulin, inhibiting the assembly of tubulin into microtubules (M phase of the cell cycle). They are derived from the Madagascar periwinkle, *Catharanthus roseus* (formerly known as *Vinca rosea*). The *Vinca* alkaloids include: Vincristine, Vinblastine, Vinorelbine, Vindesine.

"Taxanes" are derived from the Pacific yew tree, *Taxus brevifolia*. Taxanes enhance stability of microtubules, preventing the separation of chromosomes during anaphase. Taxanes include: Paclitaxel and Docetaxel.

Below is a list of chemotherapeutic drugs (by their trademarks), including paclitaxel (Taxol®), Iressa, Gefitinib and Xyotax:

13-cis-Retinoic Acid, 2-CdA, 2-Chlorodeoxyadenosine, 5-fluorouracil 5-FU, 6-Mercaptopurine, 6-MP, 6-TG 6-Thioguanine, Abraxane, Accutane®, Actinomycin-D, Adriamycin®, Adrucil Agrylin®, Ala-Cort®, Aidesleukin, Alemtuzumab, ALIMTA, Alitretinoin, Alkaban-AQ®, Alkeran®, All-transrelinoic acid, Alpha interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic trioxide, Asparaginase, ATRA, Avestin®, Azacitidine BCG, BCNU, Bevacizumab, Bexarotene, BEXXAR®, Bicalutamide, BiCNU, Blenoxane®, Bleomycin, Bortezomib, Busulfan, Busuifex®, C225, Calcium Leucovorin, Campath®, Camptosar®, Camptothecin-11, Capecitabine, Carac™, Carboplatin, Carmustine, Carmustine wafer, Casodex®, CC-5013, CCNU (o), CDDP (t), CeeNU (t), Cerubidine (t) cetuximab, Chlorambucil, Cisplatin, Citrovorum Factor, Cladribine, Cortisone, Cosmegen (t), CPT-11 (o), Cyclophosphamide, Cytadren (t), Clarabine, Cybarabine liposomal, Cytosar-U (t). Cytoxan®, Dacarbazine, Dactinomycin, Darbepoetin alfa, Daunomycin, Daunorubicin, Daunorubicin hydrochloride (t), Daunorubicin liposomal, DaunoXome (t), Decadron, Delta-Cortef (t), Deltasone (t), Deniteukin, diftitox, DepoCyt (t), Dexamethasone, Dexamethasone acetate, dexamethasone sodium phosphate, Dexasone (t), Dexrazoxane. DHAD (o), DIC (l), Diodex (t), Docetaxel, Doxil (t), Doxorubicin, Doxorubicin liposomal, Droxia (t), DTIC, DTIC-Dome (t), Duralone (t), Efudex (t), Eligard (t), Ellence (t), Eloxatin (t), Elspar (t), Emcyt (t), Epirubicin, Epoetin alfa, Erbitux, Eriotinib, Erwinia L-asparaginase (t), Estramustine, Etnyol, Etopophos (t), Etoposide, Eloposide phosphate (t), Eulexin (t), Evista (t), Exemestane, Fareston (t), Faslodex (t), Femara®, Filgrastim, Floxuridine, Fludara (t), Fluderabine, Fluorplex (t), Fluorouracil. Fluotouracil (cream), Fluoxymesterone, Flutamide, Folinic Acid (o), FUDR (t), Fulvestrant, G-CSF (t), Gefitinib, Gemecitabine, Gemtuzumab ozogamicin, Gemzar (t), Gleevec™, Gliadel wafer (t), GM-CSF (o), Goserelin, granulocyte—colony stimulating factor (l), Granulocyte macrophage colony stimulating factor (o), Halotestin (t), Herceptin (t), Hexadrol (t), Hexalen (t), Hexamethylmelamine (l), HMM (t), Hycamtin (t), Hydrea (t), Hydrocort Acetate (t), Hydrocortisone, Hydrocortisone sodium phosphate, Hydrocortisone sodium succinate, Hydrocortone phosphate (t), Hydroxyurea, Ibritumomab, Ibritamomab Tiuxetan, Idamycin®, Idarubicin Iflex®, IFN-alpha, Ifosfamide, 1L-11, 1L-2, Imatinib mesylate, Imidazole Carboxamide, Interferon elfa, Interferon Ala-2b (PEG conjugate) (o), Interleukin-2(t), Intertetikin-11 (o), intron A® (interferon alfa-2b), Iressa®, Irinotecan, Isotretinoin, Kidrolase (t), Lanacort (t), L-asparaginase (t), LCR (o), Lenalidomide, Letrozole, Leucovorin, Loukeran (t), Leukine (t), Leuprolide, Leurocristine (o), Leustatin (t), Liposomal Ara-C (t), Liquid Pred (t), Lomustine, L-PAM (o), L-Sarcolysin (o), Lupron (t), Lupron Depot (t), Matulane (t), Maxidex (t), Mechlorethamine, Mechlorethamine Hydrochloride, Medralone (t), Medrol®, Megace (t), Megestrol, Megestrol Acetate (o), Melphalan, Mercaptopurine, Mesna, Mesnex (t), Methotrexate, Methotrexate Sodium (a), Methylprednisolone, Meticorten (t), Mitomycin, Mitomycin-C (o), Mitoxantrone, M-Prednisol (t), MTC (a), MTX (o), Mustargen (t), Mustine, Mutamycin (t), Myteran (t), Mylocel (t), Mylotarg (t), Navelbine, Nelarabine, Neosar (t), Neulasta (t), Neumega (t). Neupogen (t), Nexavar®, Nilandron (t), Nilutamide, Nipent®, Nitrogen Mustard (o), Novaldex (t), Novantrone (t), Octreotide, Octreiatide acetate (o), Oncaspar (t), Oncovin (t), Ontak (t), Onxal (t), Oprevelkin, Oraprad (t), Orasone (t), Oxaliplatin, Paclitaxel, Paclitaxel Protein-bound, Pamidronate, Panretin (t), Paraplatin (t), Pediapred (t), PEG Interferon, Pegaspargase, Pegfilgrastim, PEG-INTRON (t), PEG-L-asparaginase, PEMETREXED, Pentostatin, Phenylalanine Mustard (o). Platinol (t), Platinol-AQ (t), Prednisolone, Prednisone, Prelone (t), Procarbazine, PROCRIT®, Proleukin (t), Prolifeprospan 20 with Carmustine implant (t), Purinethol (t). Raloxilfene, Revlimid®, Rheumetrex (t), Rituxan (t), Rituximab, Roferon-A®, (interferon alfa-2a) Rubex (t), Rubidomycin hydrochloride (t), Sandostatin®, Sandostatin LAR (t), Sargramostim, Solu-Cortef (t), Solu-Medrol (t), Sorafenib, ST1-571, Streptozocin, SU11248, Sunitinib, Sutent®, Tamoxifen, Tarceva®, Targretin (t), Taxol®, Taxotere (t), Temodar®, Temozolomide, Teniposide, TESPA (o), Thalidomide, Thalomid®, TheraCys (t), Thioguanine, Thioguanine Tabloid (t), Thiophosphoamide (o), Thioplex (t), Thiotepa, TICE®, Toposar (t), Topotecan, Toremifena, Tositumomab, Trastuzumab, Tretinoin. Trexati (t), Trisenox (t), TSPA VCR (o), Valban (t), Velcade®, VePesid (t), Vesanoid (t), Viadur (t), Vidaza (t), Vinblastine, Vinblastine Sulfate (o), Vincasar Pfs (t), Vincristine, Vinorelbine, Vinorelbine tartrate (o), VLB (o), VM-26 (o), VP-16 (t), Vumon (t), Xeroda®, Xyotax, Zunosar (t), Zevalin™, Zinecard (t), Zoladex®, Zoledronic acid, Zomela®.

In addition there is another list of drugs used in cancer-therapy (mostly as chemotherapeutics):

(as trademarks): Aldara, Alimta, Androcur, Armidex, Borea, Caelyx, Campto, Casodex, Decapeptyl, Eloxatin, Eutirox, Faslodex, Ferrara, Gemzar, Gonapeptyl, Grisetin, Herceptin, Isoverin, Lysodren, Megefren, Metvix, Navelbine, Novaldex, Novantrone, Paraplatin, Procrin, Prostacur, Suprefact, Tamoxifeno Funk, Taxol, Taxotere, Testex, Elmu/Prolongatum, Tomudex, Utefos, Vepesid, Xeloda, Zoladex;

(as active compounds): Anastrozole, Bilcalutamide, Buserefline, Capecetabine, Cisplalin, Carboplatin, Desoxorubicin, Docetaxel, Etoposid, Fulvestrant, Gemcitabine, Gosereline, Irinotecan, Letrozole, Leuproroline, Megestrol, Mitotane, Mifoxantrone, Oxaliplatin, Paclitaxel, Pemetrexed, Raltitrexed, Tamoxiphen, Tegafur, Triptoreline, Vincristine, Vinblastine, Vinorelbine, Vindesine.

Paclitaxel (Taxol®) is one of the most effective and commonly used antineoplastic drugs for the treatment of solid tumours. It has two serious side effects, myelosupression and peripheral neurotoxicity. Granulocyte colony-stimulating factor effectively counteracts the noutrepenia in most patients. Unfortunately, there are no acceptable therapies to prevent or minimize the nerve damage, making neurotoxicity a significant dose-limiting side effect (Rowinsky et al., 1993a, b; Wasserheit et al., 1996; Gordon et al., 1997). Paclitaxel-induced neurotoxicity typically presents as a sensory neuropathy, with the most common complaints being numbness, tingling, burning pain and cold allodynia (Rowinsky et al., 1993a; Chaudhry et al., 1994; Forsyth et al., 1997; Dougherty et al., 2004). Sensory symptoms usually start symmetrically in the feet, but sometimes appear simultaneously in both hands and feet (Rowinsky et al., 1993a; Quasthroff and Hartung, 2002). A clinically significant number of patients with paclitaxel-induced neuropathy experience neuropathic pain. For example, in a study of 27 patients treated with paclitaxel-induced neuropathy experience neuropathic pain. For example, in a study of 27 patients treated with paclitaxel doses 135, 175 and 250-300 mg/m$^2$, neuropathic symptoms occurred in 50, 79 and 100% of patients, progressing to dose-limiting neurotoxicity in 0, 21 and 71% of patients, respectively (Postma et al., 1995).

"Neuropathic pain" is defined by the IASP as "pain initiated or caused by a primary lesion or dysfunction in the nervous system" (IASP, classification of chronic paid, $2^{nd}$ edition, IASP Press (2002), 210). For the purpose of this invention included under this heading or to be treated as synonymous is "Neurogenic Pain" which is defined by the IASP as "pain initiated or caused by a primary lesion, dysfunction or transitory perturbation in the peripheral or central nervous system". In regards to this invention the neuropathic pain treated according to this Invention is restricted to the neuropathic pain resulting from chemotherapy, meaning being caused by the use of a chemotherapeutic drug in chemotherapy. The most likely cause of this is neurotoxicity of the chemotherapeutic drug, especially peripheral neurotoxicity.

Neurotoxicity of the chemotherapeutic drug often leads to sensory neuropathy, which i.a. results in burning pain and/or cold allodynia, especially cold allodynia.

The term "analogues" as used in this application is defined here as meaning a chemical compound that is a derivative of a compound which has similar biochemical activity to that compound. For example, "Analogues" of TTX bind to the same site on the alpha subunit of sodium channels as does TTX.

The term "derivatives" as used in this application is defined here as meaning a chemical compound having undergone a chemical derivation such as substitution or addition of a further chemical group to change (for pharmaceutical use) any of its physico-chemical properties, such as solubility or bioavailability, Derivatives include so-called prodrugs, e.g. ester and ether derivatives of an active compound that yield the active compound per se after administration to a subject.

Examples of well known methods of producing a prodrug of a given acting compound are known to those skilled in the art and can be found e.g, in Krogsgaard-Larsen et al., Textbook of Drugdesign and Discovery, Taylor & Francis (April 2002).

"Sodium channel blockers" or "sodium channel blocking compounds" encompass any chemicals that bind selectively to a sodium channel and thereby deactivate the sodium channel. In particular they include chemicals which bind to the SS1 or SS2 extracellular domains of an alpha subunit of a sodium channel. Sodium channel blocking compounds that bind to the SS1 or SS2 subunit of a sodium channel, particularly tetrodotoxin and saxitoxin, are found to possess similar pharmaceutical activity (U.S. Pat. No. 6,407,088, hereby incorporated by reference).

Tetrodotoxin (alternatively in the context of this application abbreviated TTX), also known as Ti Qu Duo Xin is an alkaloid found in puffer fish (Tetradontiae). The chemical name is Octashydro-12-(Hydroxymethyl)-2-imino-5, 9, 7, 10a-dimethano-10H-[1,3]dioxocino[6,5]pyrimidine-4, 7, 10, 11, 12-pentol with a molecular formula $C_{11}H_{17}N_3O_8$ and a Molecular weight of 319.27. It is a potent non-protein neurotoxin and an indispensable tool for the study of neurobiology and physiology. Tetrodotoxin (TTX) is a marine organic toxin which is mainly found in testicles, ovaries, eggs, livers, spleens, eyeballs, and blood of puffer fish as well as in diverse animal species, including goby fish, newt, frogs and the blue ringed octopus and even in marine alga. Several processes for producing TTX are known. Usually TTX is extracted from marine organisms (e.g. JP 270719 Goto and Takahashi) but besides numerous others methods of synthesis are also described (and used for the preparation of tetrodotoxin in connection with this invention) in U.S. Pat. Nos. 6,562,191, 6,478,966, 6,562,968 or 2002/0086997, all of which are included here by reference. Tetrodotoxin is a well known compound described for example in WQ02/22129 as systemically acting as analgesic. For one of the many descriptions of TTX it is recommended turn to e.g. Tu, Anthony (Ed.) Handbook of Natural Toxins, Vol. 3: Marine Toxins and Venoms, 1988, 185-210 as well as Kao (1966), Pharmacol. Rev. 18:997-1049 and others.

The phrase "its (tetrodoxin's) derivatives" according to this invention is defined—using the definition of U.S. Pat. No. 6,030,974 (included here by reference)—as meaning amino perhydroquinazoline compounds having the molecular formula $C_{11}H_{17}N_3O_5$, "Tetrodoxin's derivatives" according to this invention encompasses compounds described in U.S. Pat. No. 5,846,975 (included here by reference) as amino hydrogenated quinazolines and derivatives including the substances set forth from column 3 line 40 to column 6 line 40. Specifically exemplified "derivatives of tetrodotoxin" according to this invention are including but are not limited to anhydro-tetrodotoxin, tetrodaminotoxin, methoxytetrodotoxin, ethoxytetrodotoxin, deoxytetrodotoxin and tetrodonic acid, 6 epi-tetrodotoxin, 11-deoxytetrodoloxin as well as the hemilactal type TTX derivatives (e.g. 4-epi-TTX, 6-epi-TTX, 11-deoxy-TTX, 4-epi-11-deoxy-TTX, TTX-8-O-hemisuccinate, chiniquitoxin, 11-nor-TTX-6(S)-ol, 11-nor-TTX-6(R)ol, 11-nor-TTX-6,6-diol, 11-oxo-TTX and TTX-11-carboxylic acid), the lactone type TTX derivatives (e.g, 6-epi-TTX (lactone), 11-deoxy-TTX (lactone), 11-nor-TTX-6(S)-ol (lactone), 11-nor-TTX-6(R)-ol (lactone), 11-nor-TTX-6,6-diol (lactone), 5-deoxy-TTX, 5,11-dideoxy-TTX, 4-epi-5,11-didroxy-TTX, 1-hydroxy-5, 11-dideoxy-TTX, 5,6,11-trideoxy-TTX and 4-epi-5,6,11-trideoxy-TTX) and the 4,9-anhydro type TTX analogs (e.g. 4,9-anhydro-TTX, 4,9-anhydro-6-epi-TTX, 4,9-anhydro-11-deoxy-TTX, 4,9-anhydro-TTX-8-O-hemisuccinate, 4,9-anhydro-TTX-11-O-hemisuccinate). The typical derivatives of TTX possess only 1/8 to 1/40 of the toxicity of TTX in mice, based upon bioassay in mice. It has been observed that these derivatives produce joint action, and do not interact adversely. Examples of TTX derivatives include novel TTX derivatives isolated from various organisms, as well as those that are partially or totally chemically synthesized (see e.g., Yotsu, M. et al. Agric. Biol. Chem., 53(3):893-895 (1989)).

"Derivatives and analogues of TTX", as referred to in the present invention, may include compounds having the general formula I wherein, $R_2$ and $R_5$ can be selected from the group consisting of H, OH, OAC, respectively;

$R_1$ call be H, or an alkyl with $C_1$-$C_4$, OH, OR, OC(O)R', $NH_2$, NHR", NR"R'", among them R can be an alkyl with $C_1$-$C_6$, R' can be an alkyl with $C_1$-$C_3$, and R", R'" can be an alkyl with $C_1$-$C_4$, respectively;

$R_3$ and $R_4$ can be =O, or when $R_3$ is H, $R_4$ can be selected from the group consisting of:
—ROH, and R is a branched or straight chain alkyl with $C_1$-$C_7$,
—CH(OH)NHOMe,
—NAP-gly,
—NAP-en,
—CH$_2$NH$_2$,
—CH$_2$NHCH$_3$,
-AAG,
—NMAG, and
-ANT;

when $R_3$ is OH or OC(O)R and R is an alkyl with $C_1$-$C_3$, $R_4$ can be selected from the group consisting of:
—CHO,
—CH$_2$-gly,
—CH$_2$-β-Ala,
—CH$_2$-Lys,
—CH$_2$-en,
—CH$_2$—NAP-Lys
—CH$_2$—NAP-en,
—CH(OH)CH(NH$_2$)COOH; and,
—NH(CH$_2$)$_n$COOH,
—NH(CH$_2$)$_n$NH$_2$; and
—NH(CH$_2$)$_n$CH(NH$_2$)COOH, wherein:
n=1-6.
en is ethylene;
NAP is 4-triazo-2-nitrobenzoic amide, indicated as formula (a);
AAG is 2-triazo-O-aminobenzoic amide, indicated as formula (b);
NMAG is O-methylaminobenzoic amide, indicated as formula (c);
ANT is O-aminobenzoic amide, indicated as formula (d);

(a)

-continued (b) [structure: benzamide with N3 and H2N substituents]

(c) [structure: benzamide with NHCH3 substituent]

(d) [structure: benzamide with NH2 substituent]

Among them, three kinds of compounds with the general formula II, III, IV are alternative.

The amino hydrogenated quinazoline compounds and derivatives thereof are compounds having following general formula II,

[structure of formula II]

wherein: $R_1$ can be selected from the group consisting of OH, an alkyl or a oxyalkyl with $C_1$-$C_4$, $NH_2$, NHR", NR"R''', among them R" and R''' can be an alkyl with $C_1$-$C_4$.

Among them, the more preferred compounds are:
Tetrodotoxin $R_S$=OH (1);
deoxytetrodotoxin $R_f$=H (2);

The amino hydrogenated quinazoline compounds and derivatives thereof are compounds having following general formula III

[structure of formula III]

wherein:
$R_3$, $R_4$ are =O, or
when $R_3$ is H, $R_4$ is selected from the group consisting of:
—$CH_2OH$,
—CH(OH)NHOMe,
—NAP-gly,
—NAP-en,
—$CH_2NH_2$,
—$CH_2NHCH_3$,
-AAG,
—NMAG, and
-ANT.

Among them, the more preferred compounds are:
AAG-degradation Tetrodotoxin $R_4$=AAG (3);
NMAG-degradation Tetrodotoxin $R_4$=NMAG (4);
ANT-degradation Tetrodotoxin $R_4$=ANT (5); and,
degradation Tetrodotoxin $R_3$, $R_4$ is =O (6).

The amino hydrogenated quinazoline and their derivatives are compounds having following general formula IV;

[structure of formula IV]

wherein, $R_4$ can be selected from the group consisting of:
—CHO,
—$CH_2$-Gly,
—$CH_2$-β-Ala,
—$CH_2$-Lys
—$CH_2$-en,
—$CH_2$—NAP-Lys
—$CH_2$—NAP-en,
—CH(OH)CH($NH_2$)COOH;
NH($CH_2$)$_4$CH($NH_2$)COOH;
—$NHCH_2COOH$;
—$NHCH_2CH_2COOH$; and
—$NHCH_2CH_2NH_2$.

Among them, the more preferred compounds are:
oxytetrodotoxin $R_4$=CHO (7);
chiriquitoxin $R_4$=CH(OH)CH($NH_2$)COOH (8);
and the compounds with the substituted groups of $R_4$:
—NH($CH_2$)$_4$ CH($NH_2$)COOH (9);
—$NHCH_2COOH$ (10);
—$NHCH_2CH_2COOH$ (11); and,
—$NHCH_2$ $CH_2$ $NH_2$ (12).

Preferably, the derivatives/analogues of tetrodotoxin comprise tetrodotoxin, anhydro-tetrodotoxin, tetrodaminotoxin. methoxytetrodotoxin, ethoxytetrodotoxin, deoxytetrodotoxin, epi-tetrodotoxin and tetrodortic acid, more preferably the derivatives/analogues of tetrodotoxin a consisting of tetrodotoxin, anhydro-tetrodotoxin, tetradaminotoxin, methoxytetrodotoxin, ethoxytetrodotoxin, deoxytetrodotoxin, epi-tetrodotoxin (4- and 6-epi-tetrodotoxin) and tetrodonic acid.

Saxitoxin (STX) and its pharmacologically acceptable salts are species of 2,6-diamino-4-((aminocarbonyl)oxy) methyl-3a.4.8,9-tetrahydro-1H, 10H-pyrrolo(1,2-o) purine-10,10-diol (3aS-(3a-a-a-4-a,10aR*)). The molecular formula of Saxitoxin is $C_{10}H_{17}N_7O_4$, it has a molecular weight of 299.3 and a general structure of:

This, and its derivatives and its analogues may be used in accordance with the disclosure. Saxitoxin is readily soluble in water and can be dispersed in aerosols. It is toxic by ingestion and by inhalation, with inhalation leading to rapid respiratory collapse and death. Chemically, saxitoxin is stable, although it can be inactivated by treatment with strong alkali. It is naturally-occurring, produced by bacteria that grow in other organisms, including the dinoflagellates *Gonyaulax catenella* and *G. tamarensis*; which are consumed by the Alaskan butter clam *Saxidomus giganteus* and the California sea mussel, *Mytilus californianeus*. The toxin can be isolated from *S. giganteus* or *M. califomianeus*. The first synthesis of STX was completed by Kishi and co-workers at Harvard in 1977 (J. Am. Chem. Soc. 1977, 99, 2818). A second synthesis was carried out by Jacobi and his collaborators whilst at Wesleyan University, Conn. (J. Am. Chem. Soc. 1984, 106, 5594). A range of alternative methods for the synthesis and purification of saxitoxin will be apparent to those skilled in the art. Analogues and derivatives of saxitoxin include but are not limited to neosaxitoxin and anhydrosaxitoxin, any other biologically active variants of the above saxitoxin structure, and pharmaceutically acceptable salts thereof.

It will be appreciated that for the purposes set out herein, tetrodotoxin, saxitoxin, and their derivatives or analogues or metabolite, can be optionally in the form of their racemate, pure stereoisomers, especially enantiomers or diastereomers or in the form of mixtures of stereoisomers, especially enantiomers or diastereomers, in any suitable ratio; in neutral form, in the form of an acid or base or in form of a salt, especially a physiologically acceptable salt, or in form of a solvate, especially a hydrate.

In this application "about" means "approximately," and illustratively, the use of the term "about" indicates that dosages slightly outside the cited ranges may also be effective and safe, and such dosages are also encompassed by the scope of the present claims.

Compounds that are "administered together with TTX" or "in combination with TTX" may be administered as part of the same composition, or may be administered separately, at the same or at separate times, in the same therapeutic regimen.

In connection with this invention "neutral form" refers either to a non-ionic form or to a neutrally net charged form, for example a Zwitter-Ion at its isoelectric point.

The term "salt" according to this invention is to be understood as meaning any form of the active compound according to the invention in which this compound assumes an ionic form or is charged and—if applicable—is also coupled with a counter-ion (a cation or anion). By this are also to be understood complexes of the active compound with other molecules and ions, in particular complexes which are complexed via ionic interactions. As preferred examples of salts this includes the acetate, monotrifluoracetate, acetate ester salt, citrate, formate, picrate, hydrobromide, monohydrobromide, monohydrochloride or hydrochloride.

The term "physiologically acceptable salt" in the context of this invention is understood as meaning a "salt" (as defined above) of at least one of the compounds according to the invention which are physiologically tolerated by humans and/or mammals.

The term "solvate" according to this invention is to be understood as meaning any form of the active compound according to the invention which has another molecule (most likely a polar solvent) attached to it via non-covalent bonding. Examples of solvates include hydrates and alcoholates, e.g. methanolate.

The term "treatment" or "to treat" in the context of this specification means administration of a compound or formulation according to the invention to prevent, ameliorate or eliminate one or more symptoms associated with neuropathic pain, hyperalgesia and/or allodynia.

Furthermore, the terms "to treat" or "treatment" according to this invention include the treatment of symptoms of neuropathic pain, hyperalgesia and/or allodynia, the prevention or the prophylaxis of the symptoms of neuropathic pain, hyperalgesia and/or allodynia, the prevention or prophylaxis causing the symptoms of neuropathic pain, hyperalgesia and/or allodynia, as well as the prevention or the prophylaxis of the consequences causing the symptoms.

According to the various embodiments, the sodium channel blockers such as TTX or STX, their analogues/derivatives or the pharmaceutical compositions comprising them, may be administered, in unit dosage form, intestinally, enterally, parenterally or topically, orally, subcutaneously, intranasally, by inhalation, by oral absorption, intravenously, intramuscularly, percutaneously, intraperitoneally, rectally, intravaginally, transdermally, sublingually, buccally, orally transmucosally. Administrative dosage forms may include the following: tablets, capsules, dragees, lozenges, patches, pastilles, gels, pastes, drops, aerosols, pills, powders, liquors, suspensions, emulsions, granules, ointments, creams, suppositories, freeze-dried injections, injectable compositions, in food supplements, nutritional and food bars, syrups, drinks, liquids, cordials etc, which could be regular preparation, delayed-released preparation, controlled-released preparation and various micro-granule delivery system, in food supplements, nutritional and food bars, syrups, drinks, liquids, cordials. In case of tablet, various carriers known in the art may be used, e.g. dilutent and resorbent such as starch, dextrin, calcium sulfate, kaolin, microcrystalline cellulose, aluminium silicate, etc; wetting agent and adhesives such as water, glycerin, polyethylene glycol, ethanol, propanol, starch mucilage, dextrin, syrup, honey, glucose solution, acacia, gelatin, carboxymethylcellulose sodium, shellac, methylcellulose, potassium phosphate, polyvinylpyrolidone, etc; disintegrating agent, such as dried starch, alginate, agar powder, laminaran, sodium bicarbonate and citric acid, calcium carbonate, polyoxyethylene sorbitol aliphatic ester, lauryl sodium sulfate, methylcellulose, ethylcellulose, lactose, sucrose, maltose, mannitol, fructose, various disaccharides and polysaccharides etc; disintegration inhibiting agent, such as sucrose, tristearin, cacao butter, hydrogenated oil, etc; absorption accelerator, such as quaternary ammonium salt, lauryl sodium sulfate, etc; lubricant, with as talc, silica, corn starch, stearate, boric acid, fluid wax, polyethylene, etc. The tablet may be further formulated into coated tablet, e.g. sugar-coated tablet, film-coated tablet, enteric-coated tablet, or double-layer tablet and multi-layer tablet. In the case of pill, various carriers known in the art may be used, e.g. dilutent and resorbent, such as glucose, lactose, starch, cacao better, hydrogenated vegetable oil, polyvinylpyrrolidone, kaolin, talc, etc; adhesives, such as acacia, bassora gum, gelatin, ethanol, honey, liquid sugar, rice paste or flour paste, etc; disintegrating agent, such as agar powder, dried starch, alginate, lauryl sodium sulfate, methylcellulose, ethylcellulose. In case of suppository, various carriers known in the art may be used, e.g. polyethylene, lecithin, cacao butter, higher alcohols, esters of higher alcohols, gelatin, semi-synthetic glyceride, etc. In the case of capsule, it may be prepared by mixing said sodium channel blockers as active ingredient with the above mentioned carriers, followed by placing the mixture into a hard gelatin capsule or soft capsule.

Also, said sodium channel blockers may be applied in the following dosage forms; microcapsules, suspension in an aqueous phase, hard capsule, or injection. In the case of injection, such as liquor, emulsion, freeze-dried injection, and suspension, all the dilutents common in the art may be used, e.g. water, ethanol, polyethylene glycol, propylene glycol, oxyethylated isostearyl alcohol, polyoxidated isostearyl alcohol, polyoxyethylene sorbitol aliphatic ester, etc. In addition, in order to obtain isotonic injection, a suitable amount of sodium chloride, glucose or glycerin may be added into the preparation, as well as regular cosolvent, buffer, pH adjusting agent, etc. In addition, coloring agent, antiseptic, perfume, correctives, food sweetening agent or other materials may be added to the pharmaceutical preparation if necessary.

In certain embodiments a formulation or pharmaceutical composition according to the invention contains the active ingredient (TTX, its derivatives and/or its analogues) as well as optionally at least one auxiliary material and/or additive and/or optionally another active ingredient.

In certain embodiments the auxiliary material and/or additive can be specifically selected from conserving agents, emulsifiers and/or carriers for parenteral application. The selection of these auxiliary materials and/or additives and of the amounts to be used depends upon how the pharmaceutical composition is to be applied. Examples include here especially parenteral like intravenous subcutaneous or intramuscular application formulations but which could also be used for other administration routes.

In certain embodiments routes of administration of tetrodotoxin its derivatives and its analogues can include intramuscular injection, intravenous injection, subcutaneous injection, sublingual, buccal, patch through skin, oral ingestion, implantable osmotic pump, collagen implants, aerosols or suppository.

In alternative embodiments the sodium channel blockers such as TTX or STX, their analogues/derivatives may be administered in a schedule of one, two, three, four, five, six, seven, eight, nine, ten, eleven, twelve, thirteen, fourteen, fifteen, sixteen, seventeen, eighteen, nineteen, twenty or more doses per day, alone or in combination with other medications, over range of time periods including but not limited to periods of one, two, three, four, five, six, seven, eight, nine, ten, eleven, twelve, thirteen, fourteen, sixteen, eighteen, twenty, twenty four, thirty, or more days; or over a period of one, two, three, four, five, six, seven, eight, nine, ten, eleven, twelve, thirteen, fourteen, sixteen, eighteen, twenty, twenty four, thirty, thirty six, forty eight, sixty, seventy two, eighty four or more months.

In particular embodiments the sodium channel blockers such as TTX or STX, their analogues/derivatives may be a voltage-gated sodium channel blocker and may bind to a SS1 or SS2 a subunit of a sodium channel. The maximum daily dose of sodium channel blocker may be up to about 10 µg, up to about 50 µg, up to about 100 µg, up to about 144 µg, up to about 150 µg, up to about 300 µg, tip to about 500 µg, up to about 750 µg, up to about 1000 µg, up to about 1250 µg, up to about 1500 µg, up to about 1750 µg, up to about 2000 µg or more. In particular embodiments the sodium channel blocker may be administered in an amount ranging between 5 and 4000 µg/day, or in ranges between 10 and 2000 µg/day, 10 and 1000 µg a day, 10 and 750 µg a day, 10 and 500 µg a day, 10 and 400 µg a day, 10 and 300 µg a day, 10 and 200 µg a day, or 10 and 100 µg/day.

In particular embodiments the daily applied dose may be from about 10 to about 160 µg, about 10 to about 140 µg, about 10 to about 120 µg, about 10 to about 100 µg, about 10 to about 90 µg, about 10 to about 80 µg, about 10 to about 70 µg, about 10 to about 60 µg, about 10 to about 50 µg, about 10 to about 40 µg, about 10 to about 30 µg, or 1 to 20 µg. In other embodiments the daily dosage of the sodium channel blacker may be about 0.1 to about 40 µg per kilogram of body weight, about 1 to about 35 µg per kilogram of body weight, about 5 to about 30 µg per kilogram of body weight, about 10 to about 30 µg per kilogram of body weight, about 15 to about 30 µg per kilogram of body weight, about 10 to about 35 µg per kilogram of body weight, or about 20 to about 40 µg per kilogram of body weight. The unit dose may be within a range of about 5 µg to about 2000 µg and may be about 5 to about 10 µg, about 10 to about 15 µg, about 15 to about 20 µg, about 20 to about 25 µg, about 25 to about 30 µg, about 30 to about 40 µg, about 40 µg to about 50 µg, about 50 µg to about 75 µg, about 75 to about 100 µg, about 100 to about 150 µg, about 150 to about 200 µg, about 200 to about 250 µg, about 250 to about 500 µg, about 500 to about 1000 µg, about 1000 to about 1500 µg or about 1500 to about 2000 µg or more than 2000 µg.

In some embodiments the dose administered is between 10 and 4000 µg/day of tetrodotoxin, its derivatives or its analogues, especially the dose of tetrodotoxin administered is normally between 10 and 4000 µg/day or—given the likely twice per day treatment—between 5 to 2000 µg each given dose, sometimes preferably between 250 and 1000 µg each given dose, sometimes preferably between 25 and 50 µg each given dose depending on the route of administration.

In some embodiments the effectiveness of a course of treatment of one, two, three. four, five or more doses or one, two or three days may last for up to about five, ten, fifteen, twenty, twenty five or thirty. In some embodiments dosing is only performed once every day or once every two, three, four, five, six, seven, eight, nine, ten, eleven, twelve, thirteen, fourteen, sixteen, eighteen, twenty, twenty four, thirty or more days.

According to the present disclosure, the dosage of said sodium channel blocker such as TTX or STX, their analogues/derivatives, depends on a variety of factors, including the nature and severity of the diseases, the sex, age, weight and individual reaction of the subject, the particular compound employed, the route and frequency of administration, etc. Said sodium channel blockers such as TTX or STX, their analogues/derivatives or the pharmaceutical compositions comprising them may be administered in single or divided dosage form, e.g. one to four doses per day. Those skilled in the art will readily understand and implement the changes to the treatment methods exemplified herein that are necessary or desirable to reflect varied therapeutic requirements.

A substance named as an "active ingredient" will have a purity of at least 97%. For example, a formulation said to have "500 μg of TTX as the active ingredient" may contain as much as 15 μg of anhydrotetrodotoxin as an impurity. On the other hand, a formulation said to have "500 μg of TTX and 500 μg of anhydrotetrodotoxin as active ingredients" will contain at least 485 μg of TTX and 485 μg of anhydrotetrodotoxin, but may contain as much as 30 μg of other substances as impurities of the active ingredients. Of course, substances named as other components of a formulation are not included when the purity of the active ingredient is considered.

In a highly preferred embodiment of the use according to the invention the neuropathic pain is peripheral neuropathic pain or peripheral neurogenic pain.

According to the IASP "peripheral neuropathic pain" is defined as "a pain initiated or caused by a primary lesion or dysfunction in the peripheral nervous system" and "peripheral neurogenic pain" is defined as "a pain initiated or caused by a primary lesion, dysfunction or transitory perturbation in the peripheral nervous system" (IASP, Classification of chronic pain, $2^{nd}$ Edition, IASP Press (2002), 213).

In another preferred embodiment of the use according to the invention the neuropathic pain is allodynia.

According to the IASP "allodynia" is defined as "a pain due to a stimulus which does not normally provoke pain" (IASP, Classification of chronic pain, $2^{nd}$ Edition, (IASP Press (2002), 210).

In another preferred embodiment of the use according to the invention the neuropathic pain is causalgia, According to the IASP "causalgia" is defined as "a syndrome of sustained burning pain, allodynia and hyperpathia after a traumatic nerve lesion, often combined with vasomotor and sudomotor dysfunction and later trophic changes" (IASP, Classification of chronic pain, $2^{nd}$ Edition, IASP Press (2002), 210).

In another preferred embodiment of the use according to the invention the neuropathic pain is hyperalgesia.

According to the IASP "hyperalgesia" is defined as "an increased response to a stimulus which is normally painful (IASP, Classification of chronic pain, $2^{nd}$ Edition, IASP Press (2002), 211).

In another preferred embodiment of the use according to the invention the neuropathic pain is hyperesthesia.

According to the IASP "hyperesthesia" is defined as "increased sensitivity to stimulation, excluding the senses" (IASP, Classification of chronic pain, $2^{nd}$ Edition, IASP Press (2002), 211).

In another preferred embodiment of the use according to the invention the neuropathic pain is hyperpathia.

According to the IASP "hyperpathia" is defined as "a painful syndrome characterized by an abnormally painful reaction to a stimulus, especially a repetitive stimulus, as well as an increased threshold" (IASP, Classification of chronic pain, $2^{nd}$ Edition, IASP Press (2002), 212).

The IASP draws the following difference between "allodynia', "hyperalgesia" and "hyperpathia" (IASP, Classification of chronic pain, $2^{nd}$ Edition, IASP Press (2002), 212);

| | | |
|---|---|---|
| Allodynia | Lowered threshold | Stimulus and response mode differ |
| Hyperalgesia | Increased response | Stimulus and response rate are the same |
| Hyperpathia | Raised threshold; Increased response | Stimulus and response rate may be the same or different |

In another preferred embodiment of the use according to the invention the neuropathic pain is neuralgia.

According to the IASP "neuralgia" is defined as "Pain in the distribution of a nerve or nerves" (IASP, Classification of chronic pain, $2^{nd}$ Edition, IASP Press (2002), 212).

In another preferred embodiment of the use according to the invention the neuropathic pain is neuritis.

According to the IASP "neuritis" is defined as "inflammation of a nerve or nerves" (IASP, Classification of chronic pain, $2^{nd}$ Edition, IASP Press (2002), 212).

In another preferred embodiment of the use according to the invention the neuropathic pain is neuropathy/neuritis.

According to the IASP "neuritis" is defined as "a disturbance of function or pathological change in a nerve: in one nerve mononeuropathy, in several nerves mononeuropathy multiplex, if diffuse and bilateral, polyneuropathy" (IASP, Classification of chronic pain, $2^{nd}$ Edition, IASP Press (2002), 212).

In another preferred embodiment of the use according to the invention the neuropathic pain is orofacial pain.

Another aspect of the present invention relates to the use of sodium channel blockers such as TTX or STX, its analogues/derivatives, optionally in the form of its racemate, pure stereoisomers, especially enantiomers or diastereomers or in the form of mixtures of stereoisomers, especially enantiomers or diastereomers. In any suitable mixing ratio; in neutral form, in the form of an acid or base or in form of a salt, especially a physiologically acceptable salt, or in form of a solvate, especially a hydrate for the production of a medicament for the treatment of allodynia developing as a consequence of Chemotherapy.

Another aspect of the present invention relates to the use of sodium channel blockers such as TTX or STX, its analogues/derivatives, optionally in the form of its racemate, pure stereoisomers, especially enantiomers or diastereomers or in the form of mixtures of stereoisomers, especially enantiomers or diastereomers, in any suitable mixing ratio; in neutral form, in the form of an acid or base or in form of a salt, especially a physiologically acceptable salt, or in form of a solvate, especially a hydrate for the production of a medicament for the treatment of hyperalgesia developing as a consequence of chemotherapy.

In a highly preferred embodiment of the invention the use according to the invention tetrodotoxin, its derivative and/or one of its analogues is used in an amount between 10 μg/day and 4 mg/day.

In a highly preferred embodiment of the invention the use according to the invention the used tetrodotoxin, its derivative or its analogue is isolated from a biological source, preferably from fish, especially puffer fish.

In a highly preferred embodiment of the invention the use according to the invention the used tetrodotoxin, its derivative or its analogue is synthesized/synthetic.

In a highly preferred embodiment of the invention at least one chemotherapeutic agent used in the chemotherapy is selected from a platin-derivative, a *Vinca* alkaloid or a taxane.

In a highly preferred embodiment of the invention at least one chemotherapeutic agent used in the chemotherapy is selected from the group consisting of cisplatin, carboplatin and oxaliplatin; vincristine, vinblastine, vinorelbine and vindesine; paclitaxel and docetaxel.

Preferably at least one chemotherapeutic agent used in the chemotherapy is cisplatin.

Preferably at least one chemotherapeutic agent used in the chemotherapy is carboplatin.

Preferably at least one chemotherapeutic agent used in the chemotherapy is oxaliplatin.

Preferably at least one chemotherapeutic agent used in the chemotherapy is vincristine.

Preferably at least one chemotherapeutic agent used in the chemotherapy is vinblastine.

Preferably at least one chemotherapeutic agent used in the chemotherapy is vinorelbine.

Preferably at least one chemotherapeutic agent used in the chemotherapy is vindesine.

Preferably at least one chemotherapeutic agent used in the chemotherapy is paclitaxel.

Preferably at least one chemotherapeutic agent used in the chemotherapy is docetaxel.

Included in this invention are especially also methods of treatment of a patient or a mammal, including men, suffering from neuropathic pain developing as a consequence of Chemotherapy using a sodium channel blocker such as tetrodotoxin or saxitoxin and/or one of its analogues or derivatives optionally in the form of its racemate, pure stereoisomers, especially enantiomers or diastereomers or in the form of mixtures of stereoisomers, especially enantiomers or diastereomers, in any suitable ratio; in neutral form, in the form of an acid or base or in form of a salt, especially a physiologically acceptable salt, or in form of a solvate, especially a hydrate. It is also preferred if the method of treatment is restricted to tetrodotoxin, and/or one of its analogues or derivatives, especially if it is restricted to tetrodotoxin, optionally in the form of its racemate, pure stereoisomers, especially enantiomers or diastereomers or in the form of mixtures of stereoisomers, especially enantiomers or diastereomers, in any suitable ratio; in neutral form, in the form of an acid or base or in form of a salt, especially a physiologically acceptable salt, or in form of a solvate, especially a hydrate. It is also preferred if the method of treatment is restricted to tetrodotoxin, in neutral form or as a salt, especially a physiologically acceptable salt, whereas preferably tetrodotoxin, its derivative and/or one of its analogues is used in an amount between 10 µg/day and 4 mg/day, is isolated from a biological source, preferably from fish, especially puffer fish, or is synthesized. It is also preferred if the method of treatment is restricted to embodiments in which at least one chemotherapeutic agent used in the chemotherapy is selected from a platin-derivative, a *Vinca* alkaloid or a taxane; especially if at least one chemotherapeutic agent used in the chemotherapy is selected from the group consisting of cisplatin, carboplatin and oxaliplatin; vincristine, vinblastine, vinorelbine and vindesine; paclitaxel and docetaxel.

Especially the above method of treatment includes also a co-treatment during chemotherapy, in which the chemotherapeutic drug/drugs are administered together with the sodium channel blocker such as tetrodotoxin or saxitoxin and/or one of its analogues or derivatives, especially TTX or in combination with sodium channel blocker such as tetrodotoxin or saxitoxin and/or one of its analogues or derivatives, especially with TTX. This co-treatment could possible happen during the whole chemotherapy, during parts of the chemotherapy, in the beginning of the chemotherapy, in the middle of the chemotherapy or at the end of the chemotherapy.

Another alternative embodiment of the present invention refers to a kit comprising TTX and/or one of its analogues or derivatives, optionally in the form of its racemate, pure stereoisomers, especially enantiomers or diastereomers or in the form of mixtures of stereoisomers, especially enantiomers or diastereomers; preferably in any suitable ratio; in neutral form in the form of an acid or base or in form of a salt, especially a physiologically acceptable salt, or in form of a solvate, especially a hydrate.

Another aspect of the invention is an active substance combination comprising (A) at least one sodium channel blocker and/or its derivatives, optionally in the form of its racemate, pure stereoisomers, especially enantiomers or diastereomers or in the form of mixtures of stereoisomers, especially enantiomers or diastereomers, in any suitable mixing ratio; in neutral form, in the form of an acid or base or in form of a salt, especially a physiologically acceptable salt, or in form of a solvate, especially a hydrate; and (B) at least one chemotherapeutic drug.

Another alternative embodiment of this invention is an active substance combination, wherein the sodium channel blocker (A) is selected from saxitoxin, its analogues and/or its derivatives; and/or tetrodotoxin, its analogues and/or its derivatives, optionally in the form of its racemate, pure stereoisomers, especially enantiomers or diastereomers or in the form of mixtures of stereoisomers, especially enantiomers or diastereomers, in any suitable mixing ratio; in neutral form, in the form of an acid or base or in form of a salt, especially a physiologically acceptable salt, or in form of a solvate, especially a hydrate;

especially the sodium channel blocker (A) is selected from tetrodotoxin, its analogues and/or its derivatives, optionally in the form of its racemate, pure stereoisomers, especially enantiomers or diastereomers or in the form of mixtures of stereoisomers, especially enantiomers or diastereomers, in any suitable mixing ratio; in neutral form, in the form of an acid or base or in form of a salt, especially a physiologically acceptable salt, or in form of a solvate, especially a hydrate;

more especially the sodium channel blocker (A) is selected from tetrodotoxin, optionally in the form of its racemate, pure stereoisomers, especially enantiomers or diastereomers or in the form of mixtures of stereoisomers, especially enantiomers or diastereomers. In any suitable mixing ratio; in neutral form, in the form of an acid or base or in form of a salt, especially a physiologically acceptable salt, or in form of a solvate, especially a hydrate.

Another alternative embodiment of this invention is an active substance combination, wherein the chemotherapeutic drug (B) is selected from a platin-derivative, a *Vinca* alkaloid or a taxane, especially the chemotherapeutic drug (B) is selected from cisplatin, carboplatin and oxaliplatin; vincristine, vinblastine, vinorelbine and vindesine; paclitaxel and docetaxel.

Another alternative embodiment of this invention is an active substance combination, wherein the sodium channel blocker (A) is selected from saxitoxin, its analogues and/or its derivatives; and/or tetrodotoxin, its analogues and/or its derivatives, optionally in the form of as racemate, pure stereoisomers, especially enantiomers or diastereomers or in the form of mixtures of stereoisomers, especially enantiomers or diastereomers, in any suitable mixing ratio; in neutral form, in the form of an acid or base or in form of a salt, especially a physiologically acceptable salt, or in form of a solvate, especially a hydrate:

especially the sodium channel blocker (A) is selected from tetrodotoxin, its analogues and/or its derivatives, optionally in the form of its racemate, pure stereoisomers, especially enantiomers or diastereomers or in the form of mixtures of stereoisomers, especially enantiomers or diastereomers, in any suitable mixing ratio;

in neutral form, in the form of an acid or base or in form of a salt, especially a physiologically acceptable salt, or in form of a solvate, especially a hydrate;

more especially the sodium channel blocker (A) is selected from tetrodotoxin, optionally in the form of its racemate, pure stereoisomers, especially enantiomers or diastereomers or in the form of mixtures of stereoisomers, especially enantiomers or diastereomers, in any suitable mixing ratio; in neutral form, in the form of an acid or base or in form of a salt, especially a physiologically acceptable salt, or in form of a solvate, especially a hydrate;

AND the chemotherapeutic drug (B) is selected from a platin-derivative, a *Vinca* alkaloid or a taxane, especially the chemotheramitic drug (B) is selected from cisplatin, carboplatin and oxaliplatin; vincristine, vinblastine, vinorelbine and vindesine; paclitaxel and docetaxel.

Another highly preferred alternative embodiment of this invention is an active substance combination, wherein the sodium channel blocker (A) is tetrodotoxin, and the chemotherapeutic drug (B) is selected from cisplatin, carboplatin and oxaliplatin; vincristine, vinblastine, vinorelbine and vindesine: paclitaxel and docetaxel, Another highly preferred alternative embodiment of this invention is an active substance combination, of tetrodotoxin and cisplatin.

Another highly preferred alternative embodiment of this invention is an active substance combination, of tetrodotoxin and carboplatin.

Another highly preferred alternative embodiment of this invention is an active substance combination, of tetrodotoxin and oxaliplatin.

Another highly preferred alternative embodiment of this invention is an active substance combination, of tetrodotoxin and vincristine.

Another highly preferred alternative embodiment of this invention is an active substance combination, of tetrodotoxin and vinblastine.

Another highly preferred alternative embodiment of this invention is an active substance combination, of tetrodotoxin and vinorelbine.

Another highly preferred alternative embodiment of this invention is an active substance combination, of tetrodotoxin and vindesine.

Another highly preferred alternative embodiment of this invention is an active substance combination, of tetrodotoxin and paclitaxel.

Another highly preferred alternative embodiment of this invention is an active substance combination, of tetrodotoxin and docetaxel.

Another highly preferred aspect of the invention is the use of a sodium channel blocker and/or its derivatives, such as TTX or STX, its analogues/derivatives, optionally in the form of its racemate, pure stereoisomers, especially enantiomers or diastereomers or in the form of mixtures of stereoisomers, especially enantiomers or diastereomers, in any suitable mixing ratio; in neutral form, in the form of an acid or base or in form of a salt, especially a physiologically acceptable salt, or in form of a solvate, especially a hydrate for the production of a medicament for the treatment of orofacial pain, preferably in the form of neuropathic pain, hyperalgesia or allodynia, more preferably in the form of neuropathic pain, hyperalgesia or allodynia, developing as a consequence of chemotherapy.

The orofacial region, the face and mouth, represent sites of some of the most common pains in the body. Epidemiological studies have revealed the high prevalence of several orofacial pain conditions such as temporomandibular disorders (TMD), burning mouth syndrome, and toothaches, (Dworkin, 2001; Feinman and Newton-John, 2004; LeResche, 2001; Lipton et al., 2001). Many of the difficulties experienced by clinicians with the management of acute and chronic orofacial pain conditions stem from a lack of recognition and understanding of their complex factors and interactions, from uncertainties of the aetiology or pathogenesis of many of the conditions, as well as from the lack of information of the comparative effectiveness of the analgesic drugs on orofacial pain.

The examples and figures in the following section describing pharmacological trials are merely illustrative and the invention cannot be considered in any way as being restricted to these applications.

EXAMPLES

Pharmacological Experiments

Experimental Group 1

Recently, models of paclitaxel-induced painful neuropathy have been developed in mice and rats. These models demonstrated that repeated administration of paclitaxel produced mechanical hyperalgesia and allodynia (Authler et al., 2000; Polomano et al., 2001; Dina et al., 2001 y 2004; Smith et al., 2004; Flatters y Bennett, 2004), cold allodynia (Polomano et al., 2001; Smith et al., 2004; Flatters y Bennett, 2004) and in some studies a thermal (warm) hyperalgesia (Polomano et al., 2001; Dina et al., 2001; Flatters y Bennett, 2004); however, other studies did not find this thermal hyperalgesia (Authier at al., 2000; Smith et al., 2004). Therefore, paclitaxel-induced painful neuropathy in rodents represents an interesting model to test the effects of drugs in neuropathic pain.

Figures:

FIG. 1: Time-course of paclitaxel induced thermal hyperalgesia, cold-allodynia and mechanical allodynia in mice. Animals were treated once daily from days 1 to 5 with paclitaxel (2 mg/kg) or its vehicle via i.p. The latency to hind paw withdrawal in the plantar test (A), the duration of hind paw licking/biting in the acetone test (B) and the threshold force for hind paw withdrawal in the Von Frey test (C) was recorded 3 days before (PRE) and at several days after the first injection of paclitaxel or its vehicle. Each animal was tested only in one nociceptive model. Each point and vertical line represents the mean±S.E.M. of the values obtained in at least 12 mice. Statistically significant differences between the values of paclitaxel- and vehicle-treated groups: * $p<0.05$; **$p<0.01$; and between the values on pre-treatment day and the days after treatment; #$p<0.05$; ##$p<0.01$ (two-way repeated measures ANOVA followed by Newman-Keuls test).

FIG. 2: Time-course of the effect of co-administration of paclitaxel+TTX (3 or 6 µg/kg) or paclitaxel+saline on latency to hind paw withdrawal in the plantar test (A), duration of hind paw licking/biting in the acetone test (B) and threshold force for hind paw withdrawal in the Von Frey test (C). Mice were treated once daily from days 1 to 5 with an s.c. injection of TTX (3 or 6 µg/kg) or saline 30 minutes before each i.p. injection of paclitaxel (2 mg/kg), The response evaluated was recorded in each animal 3 days before (PRE) and at several days after the first injection of paclitaxel+TTX or paclitaxel+saline. Each animal was tested only in one nociceptive model. Each point and vertical line represents the mean±S.E.M. of the values obtained in at least 16 animals. No statistically significant differences between the values of both groups of treatment were found in the plantar test, but only a slight tendency can be seen. Statistically significant differences in comparison to paclitaxel+saline *p<0.05, **p<0,01; and between the values on pre-treatment day and the days after treatment #p<0.05, ##p<0.01 (two-way repeated measures ANOVA followed by Newman-Keuls test).

FIG. 3: Time-course of the effect on the latency to hind paw withdrawal (plantar test) of a single s.c. injection of tetrodotoxin (TTX: 3 or 6 µg/kg) or saline in mice pre-treated with (A) paclitaxel or (B) paclitaxel-vehicle. Animals were treated once daily from days 1 to 5 with paclitaxel or its vehicle via i.p. and the day 7 received a single s.c. injection of TTX or saline. The latency to hind paw withdrawal was recorded in each animal 3 days before (PRE) and 7 days after the first injection of paclitaxel or its vehicle. This day, paw withdrawal latency was recorded immediately before (time 0) and at several times (30, 60, 90, 120 and 180 min) after the injection of TTX or saline. Each animal received either saline or one dose of TTX. Each point and vertical line represents the mean±S.E.M. of the values obtained in at least 12 animals. (A) Statistically significant differences among the values of TTX- and saline-treated groups at the same time after treatment: *p<0.05; **p<0.01; and between the values on pre-treatment day and the days after treatment: #p<0.05; ##p<0.01 (two-way repeated measures ANOVA followed by Newman-Keuls test). (B) No statistically significant differences among the values of the three groups were observed at any observation time, nor in comparison with their own pre-treatment day values (two-way repeated measures ANOVA).

FIG. 4: Time-course of the effect on the duration of hind paw licking/biting (acetone test) of a single s.c. injection of tetrodotoxin (TTX; 3 or 6 µg/kg) or saline in mice pre-treated with (A) paclitaxel or (B) paclitaxel-vehicle. Animals were treated once daily from days 1 to 5 with paclitaxel or its vehicle via i.p. and the day 14 received a single s.c. injection of TTX or saline. The duration of hind paw licking/biting was recorded in each animal 3 days before (PRE) and 14 days after the first injection of paclitaxel or its vehicle. This day, duration of hind paw licking/biting was recorded immediately before (time 0) and at several times (60, 120 and 180 min) after the injection of TTX or saline. Each animal received either saline or one dose of TTX. Each point and vertical line represents the mean±S.E.M. of the values obtained in at least 12 animals. (A) Statistically significant differences among the values of TTX- and saline-treated groups at the same time after treatment: **p 0.01; and between the values on pre-treatment day and the days after treatment: ##p<0.01 (two-way repeated measures ANOVA followed by Newman-Keuls test). (B) No statistically significant differences between the values of the two groups were observed at any observation time, nor in comparison with their own pre-treatment day values (two-way repeated measures ANOVA).

FIG. 5: Time-course of the effect on the threshold force for hind paw withdrawal (Von Frey test) of a single s.c. injection of tetrodotoxin (TTX: 3 or 6 µg/kg) or saline in mice pre-treated with (A) paclitaxel or (B) paclitaxel-vehicle. Animals were treated once daily from days 1 to 5 with paclitaxel or its vehicle via i.p. and the day 10 received a single s.c. injection of TTX or saline. The threshold force for hind paw withdrawal was recorded in each animal 3 days before (PRE) and 10 days alter the first injection of paclitaxel or its vehicle. This day, paw withdrawal latency was recorded immediately before (time 0) and at several times (30. 60, 90, 120 and 180 min) after the injection of TTX or saline. Each animal received either saline or one dose of TTX. Each point and vertical line represents the mean±S.E.M, of the values obtained in at least 12 animals. (A) Statistically significant differences among the values of TTX- and saline-treated groups at the same time after treatment ** p<0.01; and between the values on pre-treatment day and the days after treatment: ##p<0.01 (two-way repeated measures ANOVA followed by Newman-Keuls test). (B) No statistically significant differences among the values of the three groups were observed at any observation time, nor in comparison with their own pre-treatment day values (two-way repeated measures ANOVA).

Methods:

In General:

Experiments were performed in CD-1 mice (Charles River, S. A) with n=10/experimental group. Paclitaxel-induced painful peripheral neuropathy was produced by i.p. administration of paclitaxel once daily during two weeks as previously described (Dina et al., 2001), control animals received the same volume of solvent (a mixture of ethanol and erernophor EL)

Mechanical hyperalgesia and allodynia was evaluated with Von Frey filaments and a Randall-Sellito paw-pressure analgesymeter (Dina et al., 2001; Flatters and Bennet, 2004), cold allodynia was evaluated using the acetone drop method (Polomano et al., 2001; Smith et al., 2004), whereas thermal hyperalgesia was measured with the Hargreaves method (Dina et al., 2001; Polomano et al., 2001).

TTX exerted clear analgesic effects in this model of neuropathic pain.

TTX was injected s.c. immediately before each paclitaxel injection to test whether TTX affect the development of the painful peripheral neuropathy or in the third week (when paclitaxel injection have ended and the neuropathy is fully developed) to test whether TTX interferes with the expression of the different signs of paclitaxel-induced neuropathic pain.

Specific Description:

Animals. Female CD-1 mice weighing 25-30 g were used. The animals were housed in colony cages with free access to food and water prior to the experiments. They were maintained in temperature- and light-controlled rooms (22±1° C., lights on at 08.00 h and off at 20.00 h, air replacement every 20 min). Testing took place during the light phase (from 9.00 h to 15.00 h). Paclitaxel was dissolved in a solution made up of 50% Cremophor EL and 50% absolute ethanol to obtain a concentration of 6 mg/ml. This paclitaxel solution was conserved at −20° C. during a maximum of 14 days and was diluted in normal saline (NaCl 0.9%), just before administration, to a final concentration of 2 mg/10 ml. The vehicle of paclitaxel was diluted at the time of injection with saline (NaCl 0.9%) in the same proportion as the paclitaxel solution.

Paclitaxel (2 mg/kg) was administered intraperitoneously (i.p.), in a volume of 10 ml/kg, once per day for five consecutive days. Therefore, the cumulative dose was 10 mg/kg per mouse. In the control group the vehicle of paclitaxel was administered following the same schedule.

TTX base solution (concentration of 15 µg/ml), was diluted in normal saline just before administration to final concentrations of 3 and 6 µg/5 ml. The injection of TTX (3 or 6 µg/kg) or its solvent (normal saline) was administered subcutaneously (s.c.) in the interscapular area, using an injection volume of 5 ml/kg.

The effects of s.c. TTX on paclitaxel-induced neuropathic pain were examined in two different ways. To evaluate the effect of TTX on the development of paclitaxel-induced pain, the animals received firstly a s.c. infection of TTX 30 min before each i.p, injection of paclitaxel for five consecutive days. Posteriorly the response of the animals to the different nociceptive stimuli was tested during 2-4 weeks, depending on the test (see below), without any additional treatment. Each animal was tested only in one nociceptive model. To test the effect of TTX on the expression of paclitaxel-induced pain a single TTX injection was performed the day of maximum expression of thermal hyperalgesia (day 7 from the beginning of paclitaxel administration), mechanical allodynia (day 10) or cold allodynia (day 14) (sea results for details). Each animal received only one dose of TTX and was tested in only one nociceptive model.

Procedure for assessment of heat hyperalgesia. Thermal hyperalgesia was assessed by the following method; Mice were habituated in individual Plexiglas chambers (7×7×22 cm), placed atop a glass floor, during two hours. During this time, mice initially exhibited exploratory behaviour but subsequently stopped exploring and stood quietly with occasional bouts of grooming. After habituation, a beam of radiant heat was focused to the plantar surface of the hind paws, using a plantar test apparatus (Ugo Basile, Comerio, Italy), until the mouse made a withdrawal response. The nocifensive withdrawal reflex interrupts the light reflected from the paw onto a photocell and automatically turns off the light and a timer. Therefore, the latency to withdrawal value (that indirectly indicated the heat-pain threshold) was automatically recorded. The intensity of the light was adjusted at the start of the experiments such that average baseline latencies were about 8 s. This intensity was never changed. Each mouse was tested three times alternately on each hind paw and the latencies for both paws were averaged together in each measurement time, At least, one minute was allowed between consecutive same paw attempts. A cut-off latency time of 16 seconds was imposed in each measurement in order to avoid lesions to the skin and unnecessary suffering to the animals, To elucidate the time-course of paclitaxel-induced heat hyperalgesia in control mice, pretreatment baseline latencies were obtained three days before drug treatment. Then, animals were treated with paclitaxel or its vehicle once daily during 5 days. Posttreatment latencies were assessed on days 7, 10, 14 and 17 after the first injection of paclitaxel. When the effect of TTX on the development of paclitaxel-induced heat hyperalgesia was tested, the procedure was the same except that TTX or its solvent was s.c. injected 30 min before each daily dose of paclitaxel or its vehicle (i.p.) during the 5 days of treatment. The effect of TTX on the expression of paclitaxel-induced heat-hyperalgesia was tested on day 7 after the first injection of paclitaxel, since the maximum heat hyperalgesia was observed that day. Therefore, on day 7, after the habituation period to the apparatus, baseline latencies were recorded and immediately later TTX or its solvent was injected s.c., paw withdrawal latencies were assessed again 30, 60, 90, 120 and 180 minutes after the injection. Around 9% of the animals treated with paclitaxel did not developed thermal hyperalgesia the day 7 after paclitaxel-treatment. These animals were not used to evaluated the effect of TTX on the expression of paclitaxel-induced thermal hyperalgesia.

Procedure for assessment of cold allodynia. Cold allodynia was tested as previously described by Smith et al., 2004. by gently touching the plantar skin of the hind paws with an acetone bubble formed with a syringe connected to a thin polyethylene tube. The mice were housed and habituated for 30 min in transparent plastic boxes (7×7×13 cm) with a floor made of wire mesh. After the adaptation period, acetone was applied alternately three times to each paw at intervals of 30 s, and the duration and frequency of licking or biting were recorded. A small mirror was placed behind the chambers to allow clear observation of the paws. The time spent licking or biting the paw was recorded by a stopwatch and represented as the cumulative time of licking/biting in the six measurements. Since in the experiments licking persisting more than 10 s was very unusual, a cut-off time of 10 s was used to each trial. The frequency of licking/biting was expressed as a percentage, and calculated with the following formula: (number of trials accompanied by licking or biting/total number of trials)×100.

To elucidate the time-course of paclitaxel-induced cold allodynia in control mice, the animals were tested previously to paclitaxel administration (pretreatment value) and on different days (days 7, 10, 14, 17, 21 and 24) after the first paclitaxel or vehicle injection. The same procedure was followed to test the effect of TTX on the development of cold allodynia, but in this case, TTX or its solvent was s.c. injected 30 min before each of the 5 paclitaxel i.p. injections. Because the maximum allodynia effect induced by paclitaxel was observed on days 10-14 after its first injection, the effects of TTX on the expression of cold allodynia was assessed on day 14. This day, once baseline response to acetone was recorded the animals received an s.c. injection of TTX or its solvent, and the response to acetone was recorded again at 60, 120 and 180 min after the injection. Around 33% of the control animals treated with paclitaxel did not show cold allodynia; therefore, it was differentiated between 'responders' and 'non-responders' mice in this test. The 'non-responders' mice were easily identified because they spent less than 2 s licking/biting the paw stimulated with acetone on days 7 and 10 after paclitaxel administration. The 'non-responder' animals were not used to test the effect of TTX on the expression of cold allodynia since they do not express enough cold allodynia.

Procedure for assessment of mechanical allodynia. To assess mechanical allodynia, paw withdrawal thresholds were measured using a Dynamic Plantar Aesthesiometer (Ugo Basile, Italy). The electronic Von Frey device employs a single nonflexible filament which applies a progressively increasing force (from 0 to 10 g) against the plantar surface of the hind paw over a 20 s period. The nocifensive withdrawal reflex automatically turns off the stimulus and the mechanical threshold value is showed in a screen. The day of the experiment, mice were placed individually in test compartments (9×9×14 cm) with a wire mesh bottom and allowed to acclimatize to them for 2 h. After habituation, each mouse was tested three times alternately in each hind paw.

To elucidate the time-course of paclitaxel-induced mechanical allodynia in control mice, the animals were tested previously to paclitaxel administration (pretreatment value) and on different days (days 7, 10, 14 and 17) after the first paclitaxel or vehicle injection. The same procedure was followed to test the effect of TTX on the development of paclitaxel-induced mechanical allodynia, except that TTX or its solvent was s.c. injected 30 min before each daily dose of paclitaxel or its vehicle (i.p.) during the 5 days of treatment. The effect of TTX on the expression of paclitaxel-induced mechanical allodynia was evaluated on day 10, because the maximum change of the mechanical threshold was observed on that day. Therefore, the day 10, after the habituation period to the apparatus, baseline latencies were recorded, subsequently TTX or its solvent was injected s.c. and paw withdrawal latencies were assessed again 30, 60, 90, 120 and 180 minutes after the injection. Most animals (96%) treated with paclitaxel showed a reduction of the mechanical threshold; those animals that did not show mechanical allodynia were not used to test the effect of TTX on the expression of paclitaxel-induced mechanical allodynia.

Results

Time-course of paclitaxel-induced thermal hyperalgesia, cold- and mechanical-allodynia in control mice. The values obtained on the pre-treatment day in paclitaxel- and vehicle-treated animals were not significantly different in plantar test (FIG. 1A), acetone test (FIG. 1B) and Von Frey test (FIG. 1C). Administration during 5 days of paclitaxel-vehicle did not significantly modify the response of the animals in any test at any post-treatment day in comparison to the pre-treatment value (FIGS. 1A-C). On the other hand, 5 days of treatment with paclitaxel (2 mg/kg, i.p.) significantly reduced the paw withdrawal latency values in the plantar test all the post-treatment days, in comparison to the pre-treatment day value (FIG. 1A). Paclitaxel-induced thermal hyperalgesia was maximal 7 days after the first injection of the antineoplastic (FIG. 1A); therefore, the effect of TTX on the expression of thermal hyperalgesia was evaluated on day 7.

In the acetone test, administration of paclitaxel (2 mg/kg, i.p,) once daily during 5 days permit to distinguish two groups of animals depending on their response. Most animals (67%) treated with paclitaxel significantly ($p<0,01$) increased the time spent licking/biting the paw stimulated (FIG. 1B) and the frequency of paw licking/biting all the post-treatment days, in comparison to the pre-treatment day value. These animals constitute the paclitaxel-responder animals. On the other hand, a 33% of paclitaxel-treated animals did not show cold allodynia, and their response to acetone was indistinguishable from that of animals treated with paclitaxel-vehicle in both duration (FIG. 1B) and frequency of licking/biting. When the values of these two variables among the different groups on the same day of evaluation were compared, statistically significant differences between paclitaxel-responder and the other two groups (paclitaxel-non-responder or paclitaxel-vehicle) each day of evaluation after treatment (FIG. 1B) was observed. Paclitaxel-induced cold allodynia was maximal 10-14 days after the first injection of the antineoplastic for both variables recorded (FIG. 1B); therefore, the effect of TTX on the expression of cold allodynia was evaluated on day 14.

Administration of paclitaxel (2 mg/kg, i.p., during 5 days) induced mechanical allodynia in mice, since it significantly reduced the threshold force for paw withdrawal in the Von Frey test on day 10, in comparison both with the pre-treatment day value and with the value obtained the same day in the paclitaxel-vehicle treated animals (FIG. 1C). Therefore, the effect of TTX on the expression of mechanical allodynia was tested on day 10.

Effect of tetrodotoxin (TTX) on the development of paclitaxel-induced thermal hyperalgesia, cold- and mechanical-allodynia. The pre-treatment values were similar in the two experimental groups (paclitaxel+saline and paclitaxel+TTX) in all test performed (plantar, acetone and Von Frey tests) (FIGS. 2A, 2B and 2C).

In the plantar test, the paw withdrawal latency values were significantly lower than the pre-treatment values in both experimental groups at all lines evaluated from 7 to 17 days after the first injection of paclitaxel (FIG. 2A). However, there were no significant differences between the values of paw withdrawal latency (throughout the 17 days of measurements) after the co-administration of paclitaxel+TTX 6 µg/kg in comparison to that obtained after paclitaxel+saline (FIG. 2A) and only a slight tendency can be seen. Therefore, co-administration of paclitaxel and TTX seem to have only a very limited effect on the development of thermal hyperalgesia induced by paclitaxel.

The group of animals in which paclitaxel (i.p.) and saline (s.c.) were co-administered during days 1 to 5 showed a significant increase on duration of paw licking/biting (FIG. 2B) and an increase in the frequency of paw licking/biting, which became maximum on days 10-14 after the first injection, like in the experiments where only paclitaxel was injected (FIG. 1B). On the other hand, in the animals which receive an s.c. injection of TTX (6 µg/kg) 30 min before each dose of i.p. paclitaxel during days 1 to 5, the duration and the frequency of paw licking/biting (throughout the 24 days after co-administration) were non-significantly different from that obtained on pre-treatment day (FIG. 2B). Moreover, statistically significant differences between the values obtained in both groups (paclitaxel+saline and paclitaxel+TTX 6 µg/kg) were observed on days 10 and 14 when duration of licking/biting was analysed (FIG. 2B), and on days 7, 10 and 14 when frequency of licking/biting was considered. Therefore, co-administration of paclitaxel i.p. and TTX 6 µg/kg s.c. inhibited the development of cold allodynia induced by paclitaxel. The effect of co-administration of paclitaxel with a lower dose of TTX (3 µg/kg) was also evaluated, but this dose of TTX did not significantly affect the development of paclitaxel-induced cold allodynia in the two variables evaluated.

The paw withdrawal threshold force values (Von Frey test) in paclitaxel+saline treated animals were significantly lower than the pre-treatment values on days 10 and 14 after the first injection of paclitaxel (FIG. 2C). However, there were no significant differences between the pretreatment and post-treatment values at any day in the animals treated with paclitaxel+TTX 3 or 6 µg/kg (FIG. 2C). Moreover, there were statistically significant differences between the values of paw withdrawal threshold force after the co-administration of paclitaxel with TTX 3 or 6 µg/kg in comparison to that obtained after paclitaxel with saline on days 10 and 14 (FIG. 2C). Therefore, co-administration of paclitaxel and TTX inhibited the development of mechanical allodynia induced by paclitaxel in mice.

Effect of tetrodotoxin (TTX) on the expression of paclitaxel-induced thermal hyperalgesia. The values of paw withdrawal latency in the plantar test, recorded on day 7, before the administration of TTX or saline (time 0), were significantly different from their values on pre-treatment day in all groups of animals that have been treated with paclitaxel (FIG. 3A, time 0 versus PRE); i.e., as expected, paclitaxel induced thermal hyperalgesia 7 days after its first injection. Saline administration at time 0 did not significantly modify paclitaxel-induced thermal hyperalgesia. The saline-treated mice kept all their values of paw withdrawal latency during the 3 hours after its injection non-significantly different from that at time 0; whereas, all these values were significantly different ($p<0.01$) from the latency value obtained before paclitaxel administration (PRE value) (FIG. 3A). On the other hand, the s.c. administration of TTX (3 or 6 µg/kg) inhibited paclitaxel-induced thermal hyperalgesia in a dose-dependent manner. This effect of TTX was significantly different from that of saline from 30 to 120 minutes after injection of TTX 6 µg/kg, and from 60 to 120 minutes in the group of mice treated with TTX 3 µg/kg (FIG. 3A). Therefore, acute administration of TTX inhibited the expression of paclitaxel-induced thermal hyperalgesia.

Figure 4B:
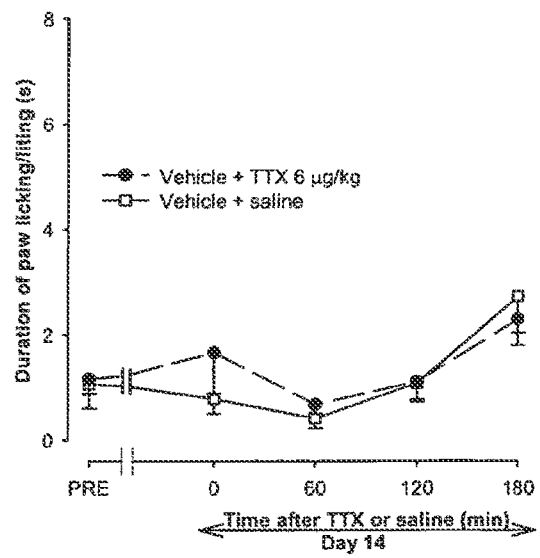
FIG. 4B is a graphical depiction of a time-course of the effect on the duration of hind paw licking/biting (acetone test) of a single s.c. injection of tetrodotoxin or saline in-mice pretreated with paclitaxel-vehicle.

As expected, 5 days of treatment with paclitaxel-vehicle did not significantly change the paw withdrawal latency value on day 7 (FIG. 3B, time 0 versus PRE). In these animals, the s.c. administration of TTX (3 or 6 µg/kg) or saline did not significantly affect paw withdrawal latency values induced by a thermal stimulus during the 3 hours of recording (FIG. 3B). Hence, TTX administration did not modify the response to a painful thermal stimulus in control animals, Effect of tetrodotoxin (TTX) on the expression at paclitaxel-induced cold allodynia. The duration and the frequency of paw licking/biting on day 14, before the treatment with TTX or saline, were significantly different from their values on pre-treatment day in all groups of animals treated during 5 days with paclitaxel (FIG. 4A, time 0 versus PRE.); i.e., as expected, paclitaxel induced a cold allodynia 14 days after its first injection. A single s.c. injection of saline on day 14 did not significantly modify the expression of paclitaxel-induced cold allodynia. The saline-treated mice kept the values of the two variables evaluated during the 3 hours after its injection non-significantly different from that at time 0; while, all these values were significantly different ($p<0.01$) from the values obtained before paclitaxel administration (PRE value) (FIG. 4A). On the other hand, the acute treatment with TTX (3 or 6 µg/kg; s.c.) inhibited the expression of paclitaxel-induced cold allodynia. This effect of TTX was significantly different from that of saline 1 h after the injection of TTX 3 or 6 µg/kg when duration of licking/biting was evaluated (FIG. 4A), and only in the animals treated with TTX 6 µg/kg when frequency of licking/biting was evaluated. As expected, treatment with paclitaxel-vehicle during 6 days did not significantly change the duration and the frequency of paw licking/biting on day 14 (FIG. 4B; time 0 versus PRE,). In these mice, the administration on day 14 of a single s.c. injection of saline or TTX (6 µg/kg) did not significantly change, in comparison to the pretreatment values, the duration (FIG. 4B) and the frequency of paw licking/biting values during the 3 h of evaluation. Therefore, the administration of paclitaxel-vehicle did not induce cold allodynia in the acetone test on day 14, and a single injection of TTX did not affect the basal response to acetone in this test.

Effect of tetrodotoxin (TTX) on the expression of paclitaxel-induced mechanical allodynia. On day 10, before the administration of TTX or saline the values of threshold force in the Von Frey test were significantly lower than the values on pre-treatment day in paclitaxel-treated group (FIG. 5A; time 0 versus PRE), i.e., as expected, the antineoplastic induced mechanical allodynia 10 days after its first injection. Saline (TTX-solvent) administration at time 0 did not significantly modify paclitaxel-induced mechanical allodynia. Mice treated with saline kept all their values of threshold force during 3 hours after its injection non-significantly different from that obtained at time 0; whereas, all values from 0 to 180 minutes were significantly different ($p<0.01$) in comparison to that obtained on pre-treatment day (FIG. 5A). On the other hand, the s.c. administration of TTX (1 and 3 µg/kg) inhibited mechanical allodynia induced by paclitaxel. This effect of TTX was statistically significant ($p<0.01$) from 30 to 90 minutes after TTX administration in both groups of TTX-treated animals (1 and 3 µg/kg) in comparison to saline-treated animals (FIG. 5A).

As expected, 5 days of treatment with paclitaxel-vehicle did not significantly change the value of the threshold force for hind paw withdrawal on day 10 (FIG. 5B, time 0 versus PRE). The subcutaneous administration of TTX (3 or 6 µg/kg, s.c.) or saline, did not significantly modify the threshold force in those animals (FIG. 5B). Therefore, TTX administration did not alter the response to a mechanical stimulus in control animals.

Discussion

It was found that acute administration of TTX inhibited the expression of paclitaxel induced heat-hyperalgesia, mechanical- and cold-allodynia in mice, and that repeated co-administration of TTX and paclitaxel prevented the development of both kinds of allodynia without clearly affecting heat-hyperalgesia References:

Alberts D S, Noel J K, Cisplatin-associated neurotoxicity; can it be prevented? Anticancer Drugs. 1995 June; 6(3); 369-83.

Authier N, Gillel J P, Fialip J, Eschalier A, Coudore F. Description of a short-term Taxol-induced nociceptive neuropathy in rats. Brain Res. 2000 Dec. 29; 887(2)239-49.

Chaudhry V, Rowinsky E K, Sartorius S E, Donehower R C, Cornblath D R. Peripheral neuropathy from taxol and cisplatin combination chemotherapy: clinical and electrophysiological studies. Ann Neurol. 1994 March; 35(3): 304-11.

Dina O A, Chen X, Reichling D, Levine J D. Role of protein kinase Cepailon and protein kinase A in a model of paclitaxel-induced painful peripheral neuropathy in the rat. Neuroscience. 2001; 108(3):507-15.

Dina O A, Parada C A, Yeh J, Chen X, McCarter G C, Levine J D. Integrin signaling in inflammatory and neuropathic pain in the rat. Eur J Neurosci. 2004 February; 19(3):634-42.

Flatters S J, Bennett G J. Ethosuximide reverses paclitaxel- and vincristine-induced painful peripheral neuropathy. Pain. 2004 May; 109(1-2):150-61.

Forsyth P A, Balmaceda C, Peterson K, Seidman A D, Brasher P, DeAngelis L. M. Prospective study of paclitaxel-induced peripheral neuropathy with quantitative sensory testing. J Neurooncol. 1997 October; 35(1):47-53.

Gordon A N, Stringer C A, Matthews C M, Willis D L, Nemunaitis J. Phase I dose escalation of paclitaxel in patients with advanced ovarian cancer receiving cisplatin: rapid development of neurotoxicity is dose-limiting. J Clin Oncol, 1997 May; 15(5):1965-73.

Polomano R C, Bennett G J. Chemotherapy-evoked painful peripheral neuropathy. Pain Med. 2001 March; 2(1):8-14.

Polomano R C, Mannes A J, Clark U S, Bennett G J. A painful peripheral neuropathy in the rat produced by the chemotherapeutic drug, paclitaxel. Pain. 2001 December; 94(3):293-304, Poslma T J, Vermorken J B, Liefting A J, Pinedo H M, Heimans J J. Paclitaxel-induced neuropathy. Ann Oncol. 1995 May; 6(5):489-94.

Quasthoff S. Hartung H P. Chemotherapy-induced peripheral neuropathy, J Neurol. 2002 January; 249(1):9-17.

Rowinsky E K, Eisenhauer E A, Chaudhry V, Arbuck S G, Donehower R C. Clinical toxicities encountered with paclitaxel (Taxol). Semin Oncol. 1993a August; 20 (4 Suppl 3):1-15

Rowinsky E K, Chaudhry V, Forastiere A A, Sartorlus S E, Ettinger D S, Grochow L B, Lubejko B G, Cornblath D R, Donehower R C. Phase I and pharmacologic study of paclitaxel and cisplatin with granulocyte colony-stimulating factor: neuromuscular toxicity is dose-limiting, J Clin Oncol. 1993b October; 11(10):2010-20.

Smith S B, Crager S E, Mogil J S, Paclitaxel-induced neuropathic hypersensitivity in mice: responses in 10 inbred mouse strains. Life Sci. 2004 Apr. 9; 74(21):2593-604.

Wasserheit C. Frazein A, Oratz R, Sorich J, Downey A, Hochster H, Chachoua A, Wernz J, Zeleniuch-Jacquotte A. Blum R. Speyer J. Phase II trial of paclitaxel and cisplatin in women with advanced breast cancer: an active regimen with limiting neurotoxicity. J Clin Oncol. 1996 July; 14(7):1993-9, Erratum in: J Clin Oncol 1996 December; 14(12):3175.

Experimental Group 2

Recently, several new animal models have been proposed to study the mechanisms underlying the development of these neuropathies, such as continuous intravenous injection of vincristine in rats and intraperitoneal (i.p.) administration of paclitaxel (Polomano et al., 2001).

Analgesic effectiveness of TTX was tested on a model of neuropathic pain induced by paclitaxel.

Figures

Figure 6A:
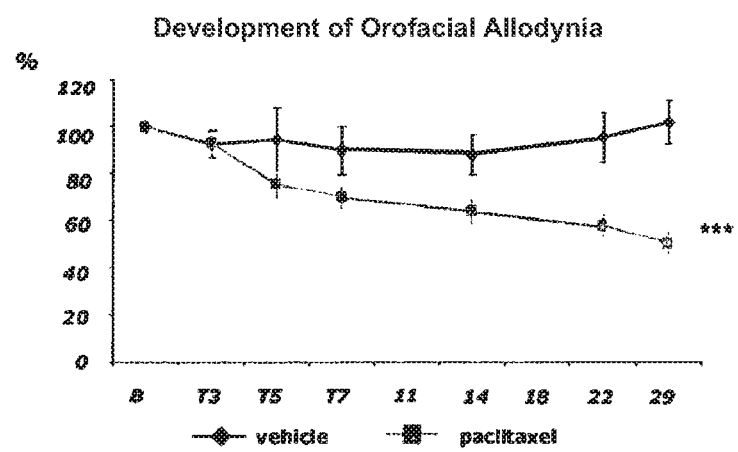
FIG. 6A is a graphical depiction of a time course of the development of allodynia after paclitaxel and paclitaxel vehicle control treatment in the orofacial region.
Figure 6B:
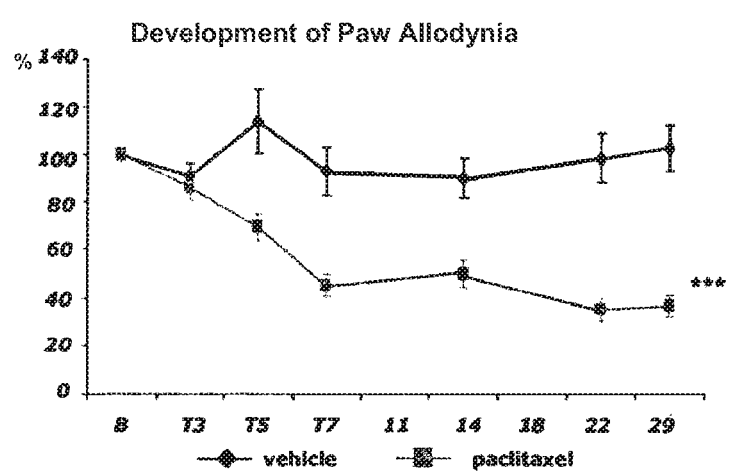
FIG. 6B is a graphical depiction of a time course of the development of allodynia after paclitaxel and paclitaxel vehicle control treatment in the paw region.
Figure 6C:
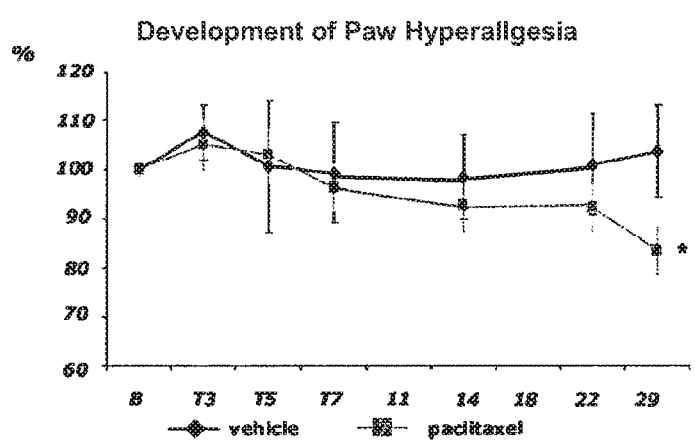
FIG. 6C is a graphical depiction of a time course of the development of hyperalgesia after paclitaxel and paclitaxel vehicle control treatment in the paw region.

FIG. 6. Development of allodynia and hyperalgesia after paclitaxel and paclitaxel vehicle control treatment in orofacial (A) and paw region (B, C). Data is expressed as the percentage (%) of the mean pre-paclitaxel control response ±SEM recorded from B (before paclitaxel treatment) to day 29, Tn=day where paclitaxel was injected. * Statistical difference vs vehicle group (*$p<0.05$, **$p<0.001$, one way ANOVA plus post hoc Bonferroni test) n=9.

Figure 7A:
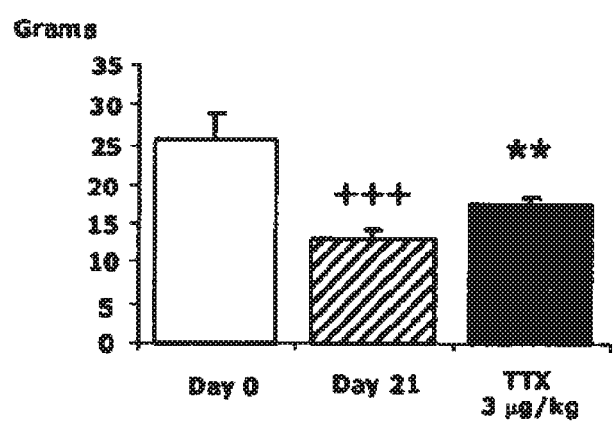
FIG. 7A is a graphical depiction of the effect of a single injection of TTX on orofacial allodynia.
Figure 7B:
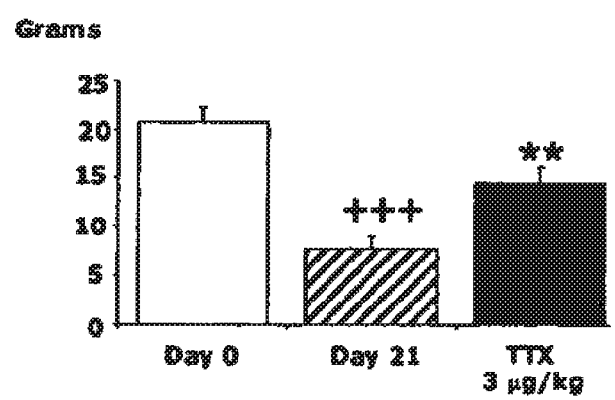
FIG. 7B is a graphical depiction of the effect of a single injection of TTX on paw allodynia.
Figure 7C:
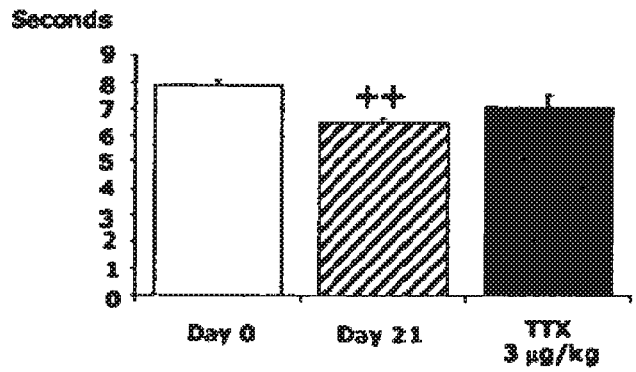
FIG. 7C is a graphical depiction of the effect of a single injection of TTX on paw hyperalgesia.

FIG. 7. Effect of a single injection of TTX on orofacial allodynia (A) paw allodynia (B) and paw hyperalgesia (C). Bars shows the mean threshold (g)±SEM recorded on day 0 (before paclitaxel treatment), on day 21 and on day 22 after paclitaxel injection. +Statistical difference vs day 0, Statistical difference vs day 21, (one way ANOVA plus post hoc Bonferroni test). *$p<0.05$, $p<0.01$, *$p<0.001$.

Figure 8:
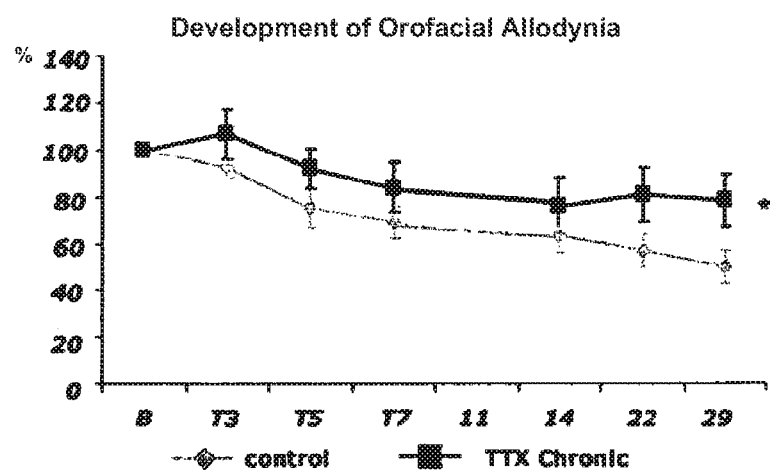
FIG. 8A is a graphical depiction of the effect of tetrodotoxin over a time course of paclitaxel-induced orofacial allodynia in control animals.
FIG. 8B is a graphical depiction of the effect of tetrodotoxin over a time course of paclitaxel-induced paw allodynia in control animals.
FIG. 8C is a graphical depiction of the effect of tetrodotoxin over a time course of paclitaxel-induced paw hyperalgesia in control animals.
Figure 8:
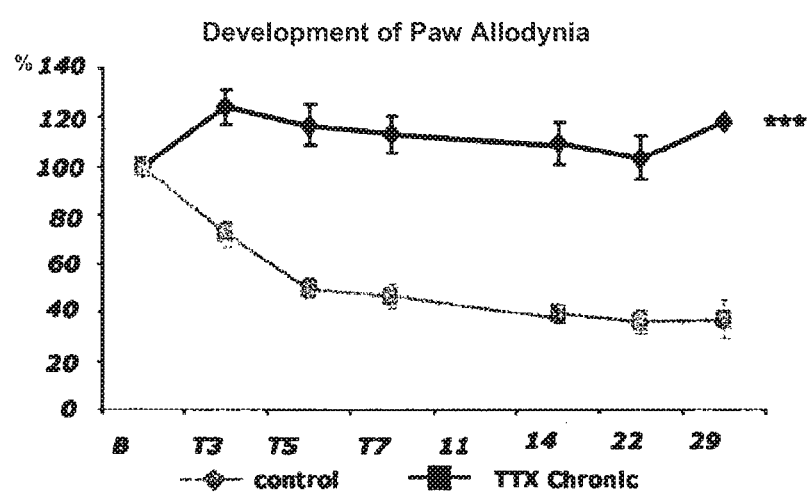
Figure 8:
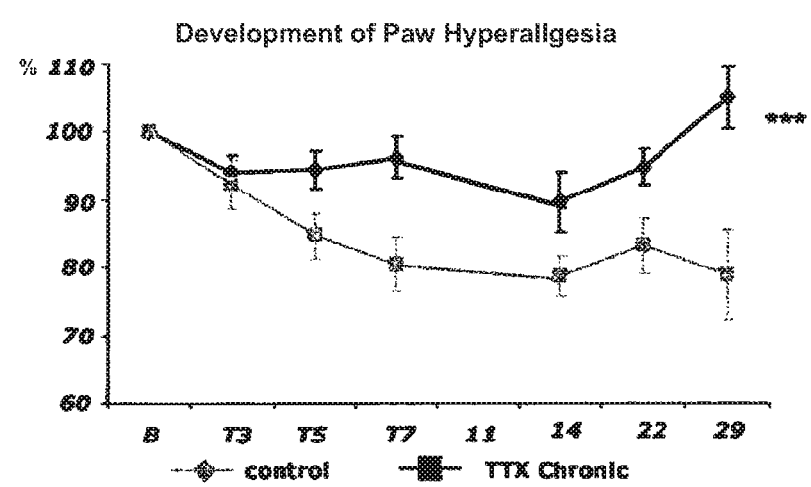

FIG. 8. Effect of TTX on time course of paclitaxel-induced allodynia in control animals. Data is expressed as the percentage of the mean pre-paclitaxel control threshold ±SEM recorded from day 0 (before paclitaxel treatment) to day 29 in control rats and in rats treated with chronic TTX, Tn=day where paclitaxel was injected. * Statistical difference vs control ('D<0.05. ***o<0.001 (one way ANOVA plus post hoc Bonferroni test) n=9.

Methods

Adult (200-250 g) male Wister rats (Harlari Iberica, Spain) were used in all the experiments. The animals were housed in clear plastic cages under Standard laboratory conditions: controlled temperature 23±1° C., 12/12-h light/dark cycle and free access to food and water. Spontaneous behaviour was observed in the cages before starting the experimental procedures, rats showing aggressiveness or alterations of the motility were discarded (2%). Number of animals per separated experimental group was at least 8.

Paclitaxel Induced Peripheral Neuropathy

After habituation to the test environment and baseline measurements of pain sensitivity (see below), animals were i.p. injected on four alternate days (days 1, 3, 5 and 7) with paclitaxel (1 mg/kg), using an injection volume of 1 ml/kg. The final cumulative paclitaxel dose administered was 4.0 mg/kg (Polomano et al., 2001). The vehicle was a mixture of saline and Cremophor EL 10%, a derivative of castor oil and ethylene oxide. This vehicle is used clinically for paclitaxel injections. Body weight was recorded (pre-treatment, and days 3. 5, 7, 13, 16, 18, 22, 24 and 29 after the first paclitaxel or vehicle administration) in the group of animals given paclitaxel (n=9) and in those treated with vehicle (n=9), Behavioral Assays Heat Hyperalgesia and Mechanical Allodynia.

The plantar surface of hind paws (sciatic nerve territory) was tested for heat-hyperalgesia and tactile-allodynia and the vibrissal zone (trigeminal nerve territory) to evaluate the effect of the administration of the different treatments.

Heat Hyperalgesia at Sciatic Nerve Territory (Hind Paw)

Heat-hyperalgesia of the hind paw was tested by measuring the latency (withdrawal time) of the hind paws from a focused beam of radiant heat applied to the plantar surface using a plantar test apparatus (Ugo Basile). Briefly, the rat was placed within a plastic compartment on a glass floor; a light source beneath the floor was aimed at the mid plantar surface of the hind paw. The withdrawal reflex interrupts the light and automatically turns off the light and a timer. The intensity of the light was adjusted at the Start of the experiment such that the control average baseline latencies were about 8 sec and a cut-off latency of 30 sec was imposed. The withdrawal latency of each paw was measured during three trials at 2 min intervals and the mean of the three readings was used for data analysis.

Tactile Allodynia at Sciatic Nerve Territory (Hind Paw)

Tactile allodynia was assessed by measuring the withdrawal threshold to calibrated von Frey hairs with intensities ranging from 0.9 to 40 g. Filaments exerting a force above 40 g were not used as they lifted the paws. On the day of the experiment animals were placed in a Perspex chamber with a mesh metal floor and allowed to acclimatize for 15 min. Starting with the lowest filament force, von Frey hairs were applied perpendicular to the mid plantar surface of both hind paws, with sufficient force to cause slight bending against the paw, and held until a response was achieved, the mechanical Stimulation was maintained for 2 seconds (maximum), this was repeated five times at an interval of 1-2 s. When the paw was sharply withdrawn, or when there was flinching upon removal of the hair, a positive response was noted; when at least 3 out of 5 responses were positive (60%), this value was accepted as tactile threshold. The process was repeated with the next higher force hair if less than 3 positive responses were noted to any hair trial.

Tactile Allodynia at Trigeminal Nerve Territory (Orofacial Region)

The effect of the paclitaxel administration in the trigeminal territory has not been previously studied. Paclitaxel was administered as previously described to test peripheral neuropathies on spinal nerves (Polomano et al., 2001).

The orofacial area was defined as the skin above the perioral (PO) skin. We measured the withdrawal threshold to calibrated von Frey hairs with intensities ranging from 0.9 to 40 g. A descending series of the filaments were used when the rat responded to the starting filament. Each filament was tested five times at an interval of a few seconds. If head withdrawal was observed at least three times after probing with a filament, the rat was considered responsive to that filament. The response threshold was defined as the lowest force of the filaments that produced at least three withdrawal responses in five tests.

Mechanical and thermal withdrawal thresholds were tested consecutively on the following groups of animals:
1. Control groups: a group injected with the paclitaxel vehicle (to control handling effects). Tests were carried out following the same schedule as their corresponding treated groups.
2. Paclitaxel treated animals: mechanical and thermal withdrawal thresholds were tested before the administration of paclitaxel (day B) and on days: 3, 5, 7, 18, 21 and 22 after starting the administration of paclitaxel. When an injection of paclitaxel had to be given on the same day as behavioural testing, rats were injected after the measurements had been taken.

After these procedures (day 22 after first administration of paclitaxel) rats received 3 μg/kg s.c. Tests were carried out 30 min after i.p. or s.c. injection. Mechanical and thermal withdrawal thresholds were tested in both paws in each group in this sequence. Tactile allodynia in the orofacial were tested at the end of the experiment.

To assess if TTX was able to prevent or reduce the development of nociceptive behaviours induced by paclitaxel, another procedure of administration was followed. Rats were simultaneously treated for one week with twice daily s.c. injections of TTX (3 μg/kg) and the usual protocol of paclitaxel administration (see above). Nociceptive behaviours were tested 3 weeks later.

3.1. Paclitaxel Induced Peripheral Neuropathy

As the effect of the repeated administration of paclitaxel on nociceptive behaviour has not been previously evaluated on the trigeminal territory, the first step was to compare the development of allodynia in the perioral region with that recorded on the hind paw (sciatic territory). FIG. 6 shows the effect of paclitaxel administration on orofacial allodynia and paw allodynia and hyperalgesia. Paclitaxel (1 mg/kg) significantly reduced the thermal latency and mechanical threshold when compared to the vehicle-treated group (FIG. 6).

To evaluate the effect of acute TTX, tactile and thermal thresholds were evaluated on days 0 (before paclitaxel), on day 21 (control of allodynia and hyperalgesia induced by paclitaxel) and on day 22 after rats were i.p. injected with the drug.

Treatment with a single dose of TTX induced a partial but significant decrease of the allodynia in the trigeminal and sciatic territories (FIG. 7A y 7B), TTX did not significantly reduce this hyperalgesia, even though a slight tendency to do so can be seen.

Finally, the simultaneous treatment with paclitaxel and TTX was able to prevent the development of allodynia in the orofacial region and in the paw as well as the hyperalgesia in the paw (FIG. 8).

Examples of Pharmaceutical Compositions

Orally Administrable Formulations

Example 1

Capsule Formulations

| Example of a formulation (A) for a Capsule | |
|---|---|
| Tetrodotoxin (TTX) (powdered material) | 0.03 mg |
| Colloidal silicon dioxide | 0.5 mg |
| Magnesium stearate | 1.0 mg |
| Lactose | 98.47 mg |
| Total | 100 mg |

| Example of a formulation (B) for a Capsule | |
|---|---|
| Tetrodotoxin (TTX) (powdered material) | 0.15 mg |
| Colloidal silicon dioxide | 0.5 mg |
| Magnesium stearate | 1.0 mg |
| Lactose | 98.35 mg |
| Total | 100 mg |

-continued

| Example of a formulation (C) for a Capsule | |
|---|---|
| Tetrodotoxin (TTX) (powdered material) | 0.3 mg |
| Colloidal silicon dioxide | 0.5 mg |
| Magnesium stearate | 1.0 mg |
| Lactose | 98.2 mg |
| Total | 100 mg |

| Example of a formulation (D) for a Capsule | |
|---|---|
| Tetrodotoxin (TTX) (powdered material) | 0.9 mg |
| Colloidal silicon dioxide | 0.5 mg |
| Magnesium stearate | 1.0 mg |
| Lactose | 97.6 mg |
| Total | 100 mg |

| Example of a formulation (E) for a Capsule | |
|---|---|
| Tetrodotoxin (TTX) (powdered material) | 0.25 mg |
| Colloidal silicon dioxide | 0.5 mg |
| Magnesium stearate | 1.0 mg |
| Lactose | 98.25 mg |
| Total | 100 mg |

| Example of a formulation (F) for a Capsule | |
|---|---|
| Tetrodotoxin (TTX) (powdered material) | 0.5 mg |
| Colloidal silicon dioxide | 0.5 mg |
| Magnesium stearate | 1.0 mg |
| Lactose | 98.0 mg |
| Total | 100 mg |

| Example of a formulation (G) for a Capsule | |
|---|---|
| Tetrodotoxin (TTX) (powdered material) | 1.0 mg |
| Colloidal silicon dioxide | 0.5 mg |
| Magnesium stearate | 1.0 mg |
| Lactose | 97.5 mg |
| Total | 100 mg |

| Example of a formulation (H) for a Capsule | |
|---|---|
| Tetrodotoxin (TTX) (powdered material) | 1.5 mg |
| Colloidal silicon dioxide | 0.5 mg |
| Magnesium stearate | 1.0 mg |
| Lactose | 97.0 mg |
| Total | 100 mg |

Example 2

Tablet Formulations

| Example of a formulation (A) for a tablet | |
|---|---|
| Tetrodotoxin (TTX) (powdered material) | 0.03 mg |
| Colloidal silicon dioxide | 0.5 mg |
| Magnesium stomata | 1.0 mg |
| Sodium croscarmelose | 5.0 mg |
| Lactose | 93.47 mg |
| Total | 100 mg |

| Example of a formulation (B) for a tablet | |
|---|---|
| Tetrodotoxin (TTX) (powdered material) | 0.15 mg |
| Colloidal silicon dioxide | 0.5 mg |
| Magnesium stearate | 1.0 mg |
| Sodium croscarmelose | 5.0 mg |
| Lactose | 93.35 mg |
| Total | 100 mg |

| Example of a formulation (C) for a tablet | |
|---|---|
| Tetrodotoxin (TTX) (powdered material) | 0.3 mg |
| Colloidal silicon dioxide | 0.5 mg |
| Magnesium stearate | 1.0 mg |
| Sodium croscarmelose | 5.0 mg |
| Lactose | 93.2 mg |
| Total | 100 mg |

| Example of a formulation (D) for a tablet | |
|---|---|
| Tetrodotoxin (TX) (powdered material) | 0.9 mg |
| Colloidal silicon dioxide | 0.5 mg |
| Magnesium stearate | 1.0 mg |
| Sodium croscarmelose | 5.0 mg |
| Lactose | 92.6 mg |
| Total | 100 mg |

| Example of a formulation (E) for a tablet | |
|---|---|
| Tetrodotoxin (TTX) (powdered material) | 0.25 mg |
| Colloidal silicon dioxide | 0.5 mg |
| Magnesium stearate | 1.0 mg |
| Sodium croscarmelose | 5.0 mg |
| Lactose | 93.25 mg |
| Total | 100 mg |

| Example of a formulation (F) for a tablet | |
|---|---|
| Tetrodotoxin (TTX) (powdered material) | 0.5 mg |
| Colloidal silicon dioxide | 0.5 mg |
| Magnesium stearate | 1.0 mg |
| Sodium croscarmelose | 5.0 mg |
| Lactose | 93.0 mg |
| Total | 100 mg |

| Example of a formulation (G) for a tablet | |
|---|---|
| Tetrodotoxin (TTX) (powdered material)) | 1.0 mg |
| Colloidal silicon dioxide | 0.5 mg |
| Magnesium stearate | 1.0 mg |
| Sodium croscarmelose | 5.0 mg |
| Lactose | 92.5 mg |
| Total | 100 mg |

| Example of a formulation (H) for a tablet | |
|---|---|
| Tetrodotoxin (TTX) (powdered material) | 1.5 mg |
| Colloidal silicon dioxide | 0.5 mg |
| Magnesium stearate | 1.0 mg |
| Sodium croscarmelose | 5.0 mg |
| Lactose | 92.0 mg |
| Total | 100 mg |

Example 3

Additional Tablet Formations

| Example of a formulation (A) for a tablet (humid Granulation) | |
|---|---|
| Tetrodotoxin (TTX) (powdered material) | 0.03 mg |
| Colloidal silicon dioxide | 0.5 mg |
| Magnesium stearate | 1.0 mg |
| POVIDONE K-30 | 5.0 mg |
| Sodium carboxymethylstarch | 5.0 mg |
| Microcrystalline cellulose | 2.0 mg |
| Lactose | 68.47 mg |
| Total | 100 mg |

| Example of a formulation (B) for a tablet (humid Granulation) | |
|---|---|
| Tetrodotoxin (TTX) (powdered material) | 0.15 mg |
| Colloidal silicon dioxide | 0.5 mg |
| Magnesium stearate | 1.0 mg |
| POVIDONE K-30 | 5.0 mg |
| Sodium carboxymethylstarch | 5.0 mg |
| Microcrystalline cellulose | 20 mg |
| Lactose | 68.35 mg |
| Total | 100 mg |

| Example of a formulation (C) for a tablet (humid Granulation) | |
|---|---|
| Tetrodotoxin (TTX) (powdered material) | 0.3 mg |
| Colloidal silicon dioxide | 0.5 mg |
| Magnesium stearate | 1.0 mg |
| POVIDONE K-30 | 5.0 mg |
| Sodium carboxymethylstarch | 5.0 mg |
| Microcrystalline cellulose | 20 mg |
| Lactose | 68.2 mg |

Example of a formulation (C) for a tablet (humid Granulation)

| | |
|---|---|
| Total | 100 mg |

Example of a formulation (D) for a tablet (humid Granulation)

| | |
|---|---|
| Tetrodotoxin (TTX) (powdered material) | 0.9 mg |
| Colloidal silicon dioxide | 0.5 mg |
| Magnesium stearate | 1.0 mg |
| POVIDONE K-30 | 5.0 mg |
| Sodium carboxymethylstarch | 5.0 mg |
| Microcrystalline cellulose | 20 mg |
| Lactose | 67.6 mg |
| Total | 100 mg |

Example of a Formulation (E) for a Tablet (Humid Granulation)

| | |
|---|---|
| Tetrodotoxin (TTX) (powdered material) | 0.25 mg |
| Colloidal silicon dioxide | 0.5 mg |
| Magnesium stearate | 1.0 mg |
| POVIDONE K-30 | 5.0 mg |
| Sodium carboxymethylstarch | 5.0 mg |
| Microcrystalline cellulose | 20 mg |
| Lactose | 68.25 mg |
| Total | 100 mg |

Example of a formulation (F) for a tablet (humid Granulation)

| | |
|---|---|
| Tetrodotoxin (TTX) (powdered material) | 0.5 mg |
| Colloidal silicon dioxide | 0.5 mg |
| Magnesium stearate | 1.0 mg |
| POVIDONE K-30 | 5.0 mg |
| Sodium carboxymethylstarch | 5.0 mg |
| Microcrystalline cellulose | 20 mg |
| Lactose | 68.0 mg |
| Total | 100 mg |

Example of a formulation (G) for a tablet (humid Granulation)

| | |
|---|---|
| Tatrodotoxin (TTX) (powdered material) | 1.0 mg |
| Colloidal silicon dioxide | 0.5 mg |
| Magnesium stearate | 1.0 mg |
| POVIDONE K-30 | 5.0 mg |
| Sodium carboxymethylstarch | 5.0 mg |
| Microcrystalline cellulose | 20 mg |
| Lactose | 67.5 mg |
| Total | 100 mg |

Example of a formulation (H) for a tablet (humid Granulation)

| | |
|---|---|
| Tetrodotoxin (TTX) (powdered material) | 1.5 mg |
| Colloidal silicon dioxide | 0.5 mg |
| Magnesium stearate | 1.0 mg |
| POVIDONE K-30 | 5.0 mg |
| Sodium carboxymethylstarch | 5.0 mg |
| Microcrystalline cellulose | 20 mg |
| Lactose | 67.0 mg |
| Total | 100 mg |

Example 4

Additional Tablet Formulations

Example of a formulation (A) for a tablet

| | |
|---|---|
| Tetrodotoxin (TTX) (powdered material) | 0.03 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (AVICEL PH-102) | 346 mg |
| Lactose monohydrate (FARMATOSE 200M) | 365.97 mg |
| Total | 800 mg |

Example of a formulation (B) for a tablet

| | |
|---|---|
| Tetrodotoxin (TTX) (powdered material) | 0.06 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (AVICEL PH-102) | 346 mg |
| Lactose monohydrate (FARMATOSE 200M) | 365.94 mg |
| Total | 800 mg |

Example of a formulation (C) for a tablet

| | |
|---|---|
| Tetrodotoxin (TTX) (powdered material) | 0.12 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (Avicel PH-102) | 346 mg |
| Lactose monohydrate (FARMATOSE 200M) | 365.88 mg |
| Total | 800 mg |

Example of a formulation (D) for tablet

| | |
|---|---|
| Tetrodotoxin (TTX) (powdered material) | 0.18 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (Avicel PH-102) | 346 mg |
| Lactose monohydrate (FARMATOSE 200M) | 365.82 mg |
| Total | 800 mg |

Example of a formulation (E) for a tablet

| | |
|---|---|
| Tetrodotoxin (TTX) (powdered material) | 0.3 mg |
| Sodium croscarmelose (AC-DI-SOL) | 40 mg |
| Colloidal silica dioxide (AEROSYL 200) | 8 mg |

| Example of a formulation (E) for a tablet | |
|---|---|
| Magnesium stearate, NF | 16 mg |
| POVIDONE K-30 | 40 mg |
| Microcrystalline cellulose (Avicel PH-102) | 346 mg |
| Lactose monohydrate (FARMATOSE 200M) | 365.7 mg |
| Total | 800 mg |

| Example of a formulation (F) for a tablet | |
|---|---|
| Tetrodotoxin (TTX) (powdered material) | 0.9 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (Avicel PH-102) | 348 mg |
| Lactose monohydrate (FARMATOSE 200M) | 365.1 mg |
| Total | 800 mg |

| Example of a formulation (G) for a tablet | |
|---|---|
| Tetrodotoxin (TTX) (powdered material) | 0.25 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (Avicel PH-102) | 346 mg |
| Lactose monohydrate (FARMATOSE 200M) | 365.75 mg |
| Total | 800 mg |

| Example of a formulation (H) for a tablet | |
|---|---|
| Tetrodotoxin (TTX) (powdered material) | 0.5 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (Avicel PH-102) | 346 mg |
| Lactose monohydrate (FARMATOSE 200M) | 365.5 mg |
| Total | 800 mg |

| Example of a formulation (I) for a tablet | |
|---|---|
| Tetrodotoxin (TTX) (powdered material) | 1.0 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (Avicel PH-102) | 346 mg |
| Lactose monohydrate (FARMATOSE 200M) | 365.0 mg |
| Total | 800 mg |

| Example of a formulation (J) for a tablet | |
|---|---|
| Tetrodotoxin (TTX) (powdered material) | 1.5 mg |
| Sodium croscarmelose (AC-DI-SOL) | 40 mg |
| Colloidal silica dioxide (AEROSYL 200) | 8 mg |
| Magnesium stearate, NF | 16 mg |
| POVIDONE K-30 | 40 mg |
| Microcrystalline cellulose (Avicel PH-102) | 346 mg |
| Lactose monohydrate (FARMATOSE 200M) | 364.5 mg |
| Total | 800 mg |

Example 5

Additional Tablet Formulations

| Example of an alternative formulation (A) for a tablet | |
|---|---|
| Tetrodotoxin (TTX) (powdered material) | 0.03 mg |
| Sodium croscarmelose (AC-DI-SOL) | 35 mg |
| Colloidal silica dioxide (AEROSYL 200) | 3 mg |
| Sodium stearate | 12 mg |
| Polyethylene glycol 8000 | 30 mg |
| Microcrystalline cellulose (Avicel PH-102) | 75 mg |
| Lactose monohydrate (FARMATOSE 200M) | 420.97 mg |
| OPADRY II ® | 24 mg |
| Total | 600 mg |

| Example of an alternative formulation (B) for a tablet | |
|---|---|
| Tetrodotoxin (TTX) (powdered material) | 0.16 mg |
| Sodium croscarmelose (AC-DI-SOL) | 35 mg |
| Colloidal silica dioxide (AEROSYL 200) | 3 mg |
| Sodium stearate | 12 mg |
| Polyethylene glycol 8000 | 30 mg |
| Microcrystalline cellulose (Avicel PH-102) | 75 mg |
| Lactose monohydrate (FARMATOSE 200M) | 420.85 mg |
| OPADRY II ® | 24 mg |
| Total | 600 mg |

| Example of an alternative forumulation (C) for a tablet | |
|---|---|
| Tetrodotoxin (TTX) (powdered material) | 0.3 mg |
| Sodium croscarmelose (AC-DI-SOL) | 35 mg |
| Colloidal silica dioxide (AEROSYL 200) | 3 mg |
| Sodium stearate | 12 mg |
| Polyethylene glycol 8000 | 30 mg |
| Microcrystalline cellulose (Avicel PH-102) | 75 mg |
| Lactose monohydrate (FARMATOSE 200M) | 420.7 mg |
| OPADRY II ® | 24 mg |
| Total | 600 mg |

| Example of an alternative formulation (D) for a tablet | |
|---|---|
| Tetrodotoxin (TTX) (powdered material) | 0.9 mg |
| Sodium croscarmelose (AC-DI-SOL) | 35 mg |
| Colloidal silica dioxide (AEROSYL 200) | 3 mg |
| Sodium stearate | 12 mg |
| Polyethylene glycol 8000 | 30 mg |
| Microcrystalline cellulose (Avicel PH-102) | 75 mg |
| Lactose monohydrate (FARMATOSE 200M) | 420.1 mg |
| OPADRY II ® | 24 mg |
| Total | 600 mg |

| Example of an alternative formulation (E) for a tablet | |
|---|---|
| Tetradotoxin (TTX) (powdered material) | 0.25 mg |
| Sodium croscarmelose (AC-DI-SOL) | 35 mg |
| Colloidal silica dioxide (AEROSYL 200) | 3 mg |
| Sodium stearate | 12 mg |
| Polyethylene glycol 8000 | 30 mg |
| Microcrystalline cellulose (Avicel PH-102) | 75 mg |
| Lactose monohydrate (FARMATOSE 200M) | 420.75 mg |
| OPADRY II ® | 24 mg |
| Total | 600 mg |

| Example of an alternative formulation (F) for a tablet | |
|---|---|
| Tetrodotoxin (TTX) (powdered Materiel) | 0.5 mg |
| Sodium croscarmelose (AC-DI-SOL) | 36 mg |
| Colloidal silica dioxide (AEROSYL 200) | 3 mg |
| Sodium stearate | 12 mg |
| Polyethylene glycol 8000 | 30 mg |
| Microcrystalline cellulose (Avicel PH-102) | 75 mg |
| Lactose monohydrate (FARMATOSE 200M) | 420.5 mg |
| OPADRY II ® | 24 mg |
| Total | 600 mg |

| Example of an alternative formulation (G) for a tablet | |
|---|---|
| Tetrodotoxin (TTX) (powdered material) | 1.0 mg |
| Sodium croscarmelose (AC-DI-SOL) | 35 mg |
| Colloidal silica dioxide (AEROSYL 200) | 3 mg |
| Sodium stearate | 12 mg |
| Polyethylene glycol 8000 | 30 mg |
| Microcrystalline cellulose (Avicel PH-102) | 75 mg |
| Lactose monohydrate (FARMATOSE 200M) | 420.0 mg |
| OPADRY II ® | 24 mg |
| Total | 600 mg |

| Example of an alternative formulation (H) for a tablet | |
|---|---|
| Tetrodotoxin (TTX) (powdered material) | 1.5 mg |
| Sodium croscemelose (AC-DI-SOL) | 35 mg |
| Colloidal silica dioxide (AEROSYL 200) | 3 mg |
| Sodium stearate | 12 mg |
| Polyethylene glycol 8000 | 30 mg |
| Microcrystalline cellulose (Avicel PH-102) | 75 mg |
| Lactose monohydrate (FARMATOSE 200M) | 419.5 mg |
| OPADRY II ® | 24 mg |
| Total | 600 mg |

Example 6

Additional Capsule Formulations

| Example of an alternative formulation (A) of a capsule | |
|---|---|
| Tetrodotoxin | 0.03 Mg |
| Colloidal silica dioxide | 0.8 mg |
| Magnesium stearate | 2.4 mg |
| Lactose | 476.77 mg |
| Total | 480 mg |

| Example of an alternative formulation (B) of a capsule | |
|---|---|
| Tetrodotoxin | 0.15 mg |
| Colloidal silica dioxide | 0.8 mg |
| Magnesium stearate | 2.4 mg |
| Lactose | 476.65 mg |
| Total | 480 mg |

| Example of an alternative formulation (C) of a capsule | |
|---|---|
| Tetrodotoxin | 0.3 mg |
| Celloidial silica dioxide | 0.8 mg |
| Magnesium stearate | 2.4 mg |
| Lactose | 476.5 mg |
| Total | 480 mg |

| Example of an alternative formulation (D) of a capsule | |
|---|---|
| Tetrodotoxin | 0.9 mg |
| Colloidal silica dioxide | 0.8 mg |
| Magnesium stearate | 2.4 mg |
| Lactose | 475.9 mg |
| Total | 480 mg |

| Example of an alternative formulation (E) of a capsule | |
|---|---|
| Tetrodotoxin | 0.25 mg |
| Colloidal silica dioxide | 0.8 mg |
| Magnesium stearate | 2.4 mg |
| Lactose | 476.55 mg |
| Total | 480 mg |

| Example of an alternative formulation (F) of a capsule | |
|---|---|
| Tetrodotoxin | 0.5 mg |
| Colloidal silica dioxide | 0.8 mg |
| Magnesium stearate | 2.4 mg |
| Lactose | 476.3 mg |
| Total | 480 mg |

| Example of an alternative formulation (G) of a capsule | |
|---|---|
| Tetrodotoxin | 1.0 mg |
| Colloidal silica dioxide | 0.8 mg |
| Magnesium stearate | 2.4 mg |
| Lactose | 475.8 mg |
| Total | 480 mg |

| Example of an alternative formulation (H) of a capsule | |
|---|---|
| Tetrodotoxin | 1.5 mg |
| Colloidal silica dioxide | 0.8 mg |
| Magnesium stearate | 2.4 mg |
| Lactose | 475.3 mg |

| Example of an alternative formulation (H) of a capsule | |
| --- | --- |
| Total | 480 mg |

Example 7

Outwardly Solid Formulations

Encapsulated Outwardly Solid Formulation (A)

| Tetrodotoxin | 60 mg |
| --- | --- |
| 0.5% dilute acetic acid | 1 ml |
| Acetic Acid-acetate buffer solution (pH = 3. | 50 ml (5% of the total volume of the prepared pharmaceutical solution |
| Water, sterile, add to | 1000 ml |

0.5 ml of this prepared solution were encapsulated in suitable consumable capsules and stored.

Encapsulated Outwardly Solid Formulation (B):

| Tetrodotoxin | 300 mg |
| --- | --- |
| 0.5% dilute acetic acid | 1 ml |
| Acetic Acid-acetate buffer solution (pH = 3. | 50 ml (5% of the total volume of the prepared pharmaceutical solution) |
| Water, sterile, add to | 1000 ml |

0.5 ml of this prepared solution were encapsulated in suitable consumable capsules and stored.

Encapsulated Outwardly Solid Formulation (C)

| Tetrodotoxin | 600 mg |
| --- | --- |
| 0.5% dilute acetic acid | 1 ml |
| Acetic Acid-acetate buffer solution (pH = 3. | 50 ml (5% of the total volume of the prepared pharmaceutical solution) |
| Water, sterile, add to | 1000 ml |

0.5 ml of this prepared solution were encapsulated in suitable consumable capsules and stored.

Encapsulated Outwardly Solid Formulation (D)

| Tetrodotoxin | 1800 mg |
| --- | --- |
| 0.5% dilute acetic acid | 1 ml |
| Acetic Acid-acetate buffer solution (pH = 3. | 50 ml (5% of the total volume of the prepared pharmaceutical solution) |
| Water, sterile, add to | 1000 ml |

0.5 ml of this prepared solution were encapsulated in suitable consumable capsules and stored.

Encapsulated Outwardly Solid Formulation (E)

| Tetrodotoxin | 500 mg |
| --- | --- |
| 0.5% dilute acetic acid | 1 ml |
| Acetic Acid-acetate buffer solution (pH = 3. | 50 ml (5% of the total volume of the prepared pharmaceutical solution) |
| Water, sterile, add to | 1000 ml |

0.5 ml of this prepared solution were encapsulated in suitable consumable capsules and stored.

Encapsulated Outwardly Solid Formulation (F)

| Tetrodotoxin | 1000 mg |
| --- | --- |
| 0.5% dilute acetic acid | 1 ml |
| Acetic Acid-acetate buffer solution (pH = 3. | 50 ml (5% of the total volume of the prepared pharmaceutical solution) |
| Water, sterile, add to | 1000 ml |

0.5 ml of this prepared solution were encapsulated in suitable consumable capsules and stored.

Encapsulated Outwardly Solid Formulation (G)

| Tetrodotoxin | 2000 mg |
| --- | --- |
| 0.5% dilute acetic acid | 1 ml |
| Acetic Acid-acetate buffer solution (pH = 3. | 50 ml (5% of the total volume of the prepared pharmaceutical solution) |
| Water, sterile, add to | 1000 ml |

0.5 ml of this prepared solution were encapsulated in suitable consumable capsules and stored.

Encapsulated Outwardly Solid Formulation (H)

| Tetrodotoxin | 3000 mg |
| --- | --- |
| 0.5% dilute acetic acid | 1 ml |
| Acetic Acid-acetate buffer solution (pH = 3. | 50 ml (5% of the total volume of the prepared pharmaceutical solution) |
| Water, sterile, add to | 1000 ml |

0.5 ml of this prepared solution were encapsulated in suitable consumable capsules and stored.

Example 8

Example of a further alternative formulation of a tablet ready to be processed into an enteric-coated formulation

| Tetrodotoxin | 0.5 mg |
| --- | --- |
| Dibasic Calcium Phosphate USP | 46.8 mg |
| Avicel PH 101 | 50.0 mg |
| NATROSOL 250 HHX | 1.0 mg |
| CAB-O-SIL M5 | 0.5 mg |
| Magnesium Stearate NF | 1.0 mg |
| Yellow Lake F D & C No 6 | 0.2 mg |
| Purified Water USP (evaporates during the process) | |
| Total | 100 mg |

Example 9

Example of an Enteric-Coated Version of Example 8

| Tablet according to Example 8 | 100 mg |
| --- | --- |
| Acryl-Eze yellow coating suspension House Std | 40.0 mg |

Example 10

Example of another form of tablet ready to be processed into a coated controlled-release formulation

| Tetrodotoxin | 0.5 mg |
| --- | --- |
| Dibasic Calcium Phosphate USP | 40.0 mg |
| Avicel PH 101 | 46.8 mg |

-continued

| | |
|---|---|
| NATROSOL 250 HHX | 10.0 mg |
| CAB-O-SIL M5 | 0.5 mg |
| Magnesium Stearate NF | 2.0 mg |
| Blue F D & C No1 | 2.0 mg |
| Purified Water USP (evaporates during the process) | |
| Total | 100 mg |

Example 11

Example of a Coated Controlled-Release Version of Example 10

| | |
|---|---|
| Tablet according to Example 10 | 100 mg |
| SURETERIC Blue suspension House Std | 20.0 mg |
| 90/10 SURELEASE/OPADRY clear suspension | 30.0 mg |

Example 12

Example of a further alternative formulation of a tablet ready to be processed into a coated formulation

| | |
|---|---|
| Tetrodotoxin | 0.5 mg |
| Dibasic Calcium Phosphate USP | 46.0 mg |
| Avicel PH 101 | 50.0 mg |
| AC-DI-SOL | 2.0 mg |
| CAB-O-SIL M5 | 0.5 mg |
| Magnesium Stearate NF | 1.0 mg |
| Purified Water USP (evaporates during the process) | |
| Total | 100 mg |

Example 13

Example of a Coated Version of Example 12

| | |
|---|---|
| Tablet according to Example 12 | 100 mg |
| OPADRY II coating suspension House Std | 20.0 mg |

Example 14

Example of a Further Alternative Formulation of a Tablet Ready to be Processed into an Enteric-Coated Formulation

| | |
|---|---|
| Tetrodotoxin | 1.0 mg |
| Dibasic Calcium Phosphate USP | 46.3 mg |
| Avicel PH 101 | 50.0 mg |
| NATROSOL 250 HHX | 1.0 mg |
| CAB-O-SIL M5 | 0.5 mg |
| Magnesium Stearate NE | 1.0 mg |
| Yellow Lake F D & C No 6 | 0.2 mg |
| Purified Water USP (evaporates during the process) | |
| Total | 100 mg |

Example 15

Example of an Enteric-Coated Version of Example 14

| | |
|---|---|
| Tablet according to Example 14 | 100 mg |
| Acryl-Eze yellow coating suspension House Std | 40.0 mg |

Example 16

Example of another form of tablet ready to be processed into a coated controlled-release formulation

| | |
|---|---|
| Tetrodotoxin | 1.0 mg |
| Dibasic Calcium Phosphate USP | 40.0 mg |
| Avicel PH 101 | 46.3 mg |
| NATROSOL 250 HHX | 10.0 mg |
| CAB-O-SIL M5 | 0.5 mg |
| Magnesium Stearate NF | 2.0 mg |
| Blue F D & C No1 | 0.2 mg |
| Purified Water USP (evaporates during the process) | |
| Total | 100 mg |

Example 17

Example of a Coated Controlled-Release Version of Example 16

| | |
|---|---|
| Tablet according to Example 16 | 100 mg |
| SURETERIC Blue suspension House Std | 20.0 mg |
| 90/10 SURELEASE/OPADRY clear suspension | 30.0 mg |

Example 18

Example of a Further Alternative Formulation of a Tablet Ready to be Processed into a Coated Formulation

| | |
|---|---|
| Tetrodotoxin | 1.0 mg |
| Dibasic Calcium Phosphate USP | 45.5 mg |
| Avicel PH 101 | 50.0 mg |
| AC-DI-SOL | 2.0 mg |
| CAB-O-SIL M5 | 0.5 mg |
| Magnesium Stearate NF | 1.0 mg |
| Purified Water USP (evaporates during the process) | |
| Total | 100 mg |

Example 19

Example of a Coated Version of Example 18

| | |
|---|---|
| Tablet according to Example 18 | 100 mg |
| OPADRY II coating suspension House Std | 20.0 mg |

With the guidance provided herein, once the required parameters of a composition or method are known, those skilled in the art will be readily able to determine the amounts and proportions of active components and other components required to manufacture a required dosage form, manufacture a kit or composition, or use the methods and compositions disclosed. The foregoing embodiments have been described in detail by way of illustration and example for purposes of clarity and understanding. As is readily apparent to one skilled in the art, the foregoing are only some of the methods and compositions that illustrate the possible embodiments. It will be apparent to those of ordinary skill in the art that a range of equivalents. variations, changes, modifications and alterations may be applied to the compositions and methods described herein without departing from the true spirit, concept and scope of the invention.

The invention claimed is:

1. A method for the prevention of neuropathic pain, developing as a consequence of chemotherapy with a chemotherapeutic agent comprising:

administering an effective amount one or more of tetrodotoxin, an analog, derivative, or pharmaceutically acceptable salt thereof, to a subject wherein the one or more of tetrodotoxin, an analog, derivative, or pharmaceutically acceptable salt thereof is administered prior to administration to the subject of at least one chemotherapeutic agent.

2. The method of claim 1, further comprising the step of co-administering a treatment of one or more of tetrodotoxin, an analog, derivative, or pharmaceutically acceptable salt thereof in combination with at least one chemotherapeutic agent.

3. The method of claim 1, wherein the one or more of tetrodotoxin, an analog, derivative, or pharmaceutically acceptable salt thereof is selected from the group consisting of tetrodotoxin, anhydro-tetrodotoxin, tetrodaminotoxin, methoxytetrodotoxin, ethoxytetrodotoxin, deoxytetrodotoxin, tetrodonic acid, 11-galactopyranosyl-tetrodotoxin, 4-olefinic-tetrodotoxin, 4-epi-tetrodotoxin, 6 epi-tetrodotoxin, 11-deoxytetrodotoxin, hemilactals of tetrodotoxin, lactones of tetrodotoxin, 4,9-anhydro tetrodotoxin, and combinations thereof.

4. The method of claim 1, wherein the one or more of tetrodotoxin, an analog, derivative, or pharmaceutically acceptable salt thereof is administered in an amount in the range from 5 µg/day to 4000 µg/day.

5. The method of claim 1, wherein the one or more of tetrodotoxin, an analog, derivative, or pharmaceutically acceptable salt thereof is administered in an amount in the range from 0.1 µg/kg/day and 40 µg/kg/day.

6. The method of claim 1, wherein the one or more of tetrodotoxin, an analog, derivative, or pharmaceutically acceptable salt thereof is administered daily in two doses.

7. The method of claim 6, wherein each dose is in an amount of between 5 µg and 2000 µg.

8. The method of claim 1, wherein the one or more of tetrodotoxin, an analog, derivative, or pharmaceutically acceptable salt thereof is isolated from a biological source.

9. The method of claim 1, wherein the one or more of tetrodotoxin, an analog, derivative, or pharmaceutically acceptable salt thereof is synthetic.

10. The method of claim 1, wherein the one or more of tetrodotoxin, an analog, derivative, or pharmaceutically acceptable salt thereof is administered subcutaneously.

11. The method of claim 1, wherein the one or more of tetrodotoxin, an analog, derivative, or pharmaceutically acceptable salt thereof is administered subcutaneously in a unit dose in the range of 5 µg to about 150 µg.

12. The method of claim 1, wherein the at least one chemotherapeutic agent is selected from the group consisting of a platinum derivative, a *Vinca* alkaloid, a taxane, cisplatin, carboplatin, oxaliplatin, vincristine, vinblastine, vinorelbine, vindesine, paclitaxel, docetaxel, and combinations thereof.

13. A method for the prevention of neuropathic pain, developing as a consequence of chemotherapy with a chemotherapeutic agent comprising:

subcutaneously administering a unit dose in the range of 5 µg to 500 µs of one or more of tetrodotoxin, an analog, derivative, or pharmaceutically acceptable salt thereof, to a subject prior to administration to the subject of at least one chemotherapeutic agent to prevent neuropathic pain, developing as a consequence of chemotherapy.

14. The method of claim 1 wherein the neuropathic pain results from peripheral neuropathy, allodynia or hyperalgesia.

15. The method of claim 13 wherein the neuropathic pain results from peripheral neuropathy, allodynia or hyperalgesia.

16. The method of claim 13 wherein the at least one chemotherapeutic agent is selected from the group consisting of a platinum derivative, a *Vinca* alkaloid, a taxane, cisplatin, carboplatin, oxaliplatin, vincristine, vinblastine, vinorelbine, vindesine, paclitaxel, docetaxel, and combinations thereof.

* * * * *